US 6,596,014 B2

(12) United States Patent
Levinson et al.

(10) Patent No.: US 6,596,014 B2
(45) Date of Patent: Jul. 22, 2003

(54) SUTURE WITH TOGGLE AND METHOD OF MANUFACTURE THEREFOR

(75) Inventors: Melvin E. Levinson, Miami, FL (US); Jesus R. Armenteros, Zona Franca de San Isidro (ES)

(73) Assignee: Scion Cardio-Vascular, Inc., Miami, FL (US)

( * ) Notice: Subject to any disclaimer, the term of this patent is extended or adjusted under 35 U.S.C. 154(b) by 0 days.

(21) Appl. No.: 09/804,764

(22) Filed: Mar. 13, 2001

(65) Prior Publication Data
US 2001/0044638 A1 Nov. 22, 2001

Related U.S. Application Data

(63) Continuation-in-part of application No. 09/661,024, filed on Sep. 13, 2000, now Pat. No. 6,319,263, which is a continuation of application No. 09/413,145, filed on Oct. 6, 1999, now Pat. No. 6,206,895.
(60) Provisional application No. 60/143,555, filed on Jul. 13, 1999.

(51) Int. Cl.[7] .................... A61L 17/00; A61B 17/04
(52) U.S. Cl. ............................................... 606/228
(58) Field of Search ............................ 606/228, 232, 606/233

(56) References Cited

U.S. PATENT DOCUMENTS

| 3,753,438 A | * | 8/1973 | Wood et al. |
| 4,006,747 A | | 2/1977 | Kronenthal et al. |
| 4,669,473 A | | 6/1987 | Richards et al. |
| 4,705,040 A | | 11/1987 | Mueller et al. |
| 4,741,330 A | | 5/1988 | Hayhurst |
| 4,744,364 A | | 5/1988 | Kensey |
| 5,046,513 A | * | 9/1991 | Gatturna et al. |
| 5,053,046 A | | 10/1991 | Janese |
| 5,807,403 A | * | 9/1998 | Beyar et al. |
| 5,860,990 A | | 1/1999 | Nobles et al. |
| 6,068,648 A | * | 5/2000 | Cole et al. |
| 6,174,324 B1 | * | 1/2001 | Egan et al. |

* cited by examiner

Primary Examiner—Ismael Izaguirre
(74) Attorney, Agent, or Firm—Robert C. Kain, Jr.; Fleit, Kain

(57) ABSTRACT

The self securing suture includes a suture having a stiff end segment at a terminal end and a toggle disposed on the terminal end such that the stiff end segment and toggle define an acute angle between 25 degrees and 65 degrees. The toggle may be a metal or a biocompatible plastic. In one embodiment, a portion of the stiffened end segment is swaged onto the toggle in a closed channel. The present invention also includes methods for producing suture toggles. One method includes creating a partial channel on a toggle, stiffening an end segment of a suture thread, positioning a portion of the stiffened end segment in the partial channel, and swaging the toggle channel closed. The toggle and swaged suture thread may be coated with a biocompatible polymer. An alternative method of manufacture includes utilizing a tubular toggle, passing the stiffened end segment through the tube and swaging the toggle tube closed. In yet another method of manufacture for producing a suture toggle, a mold is utilized to form the toggle and the stiffened, positioned suture thread end segment.

24 Claims, 18 Drawing Sheets

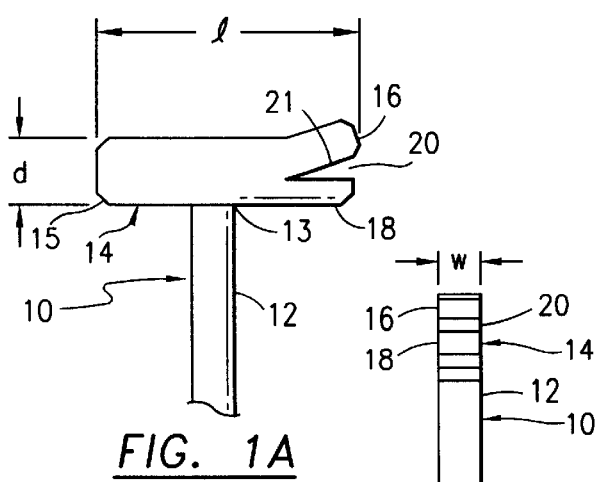
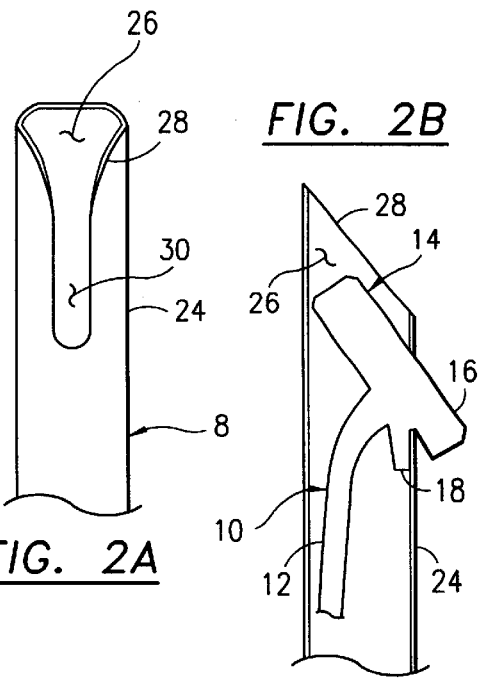
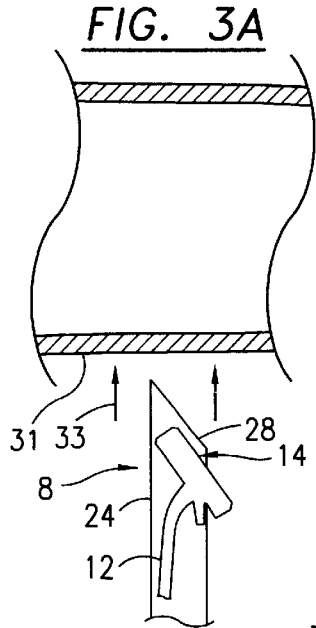
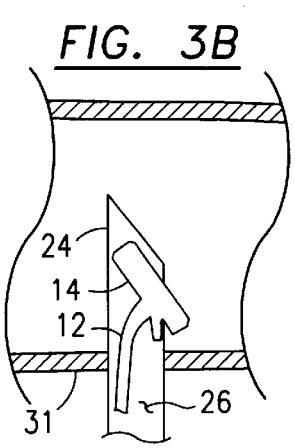
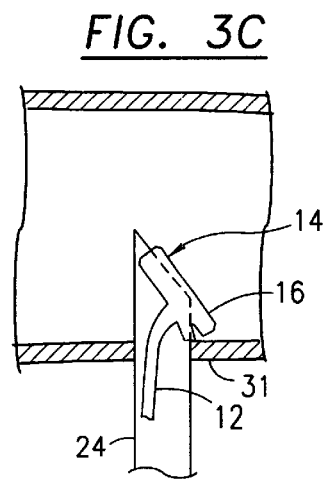
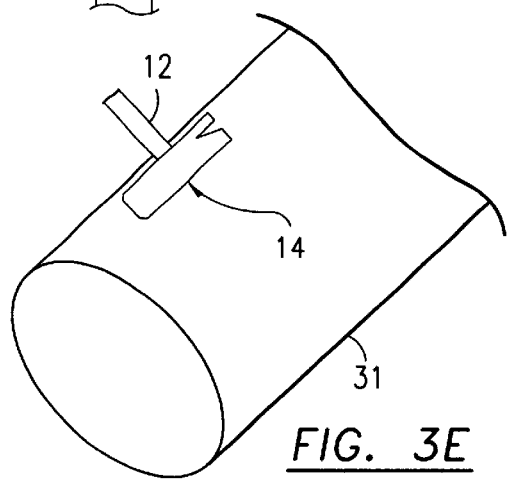
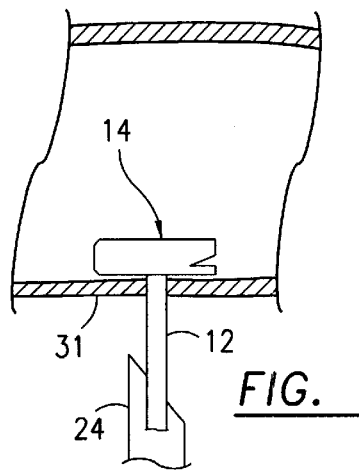

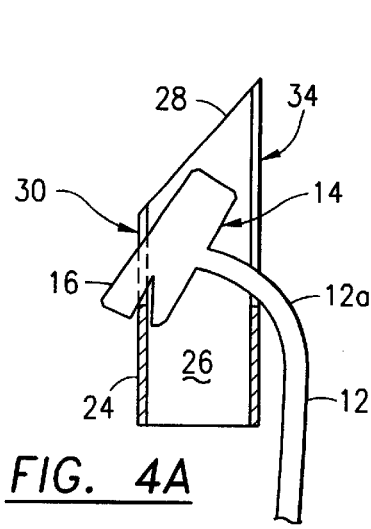
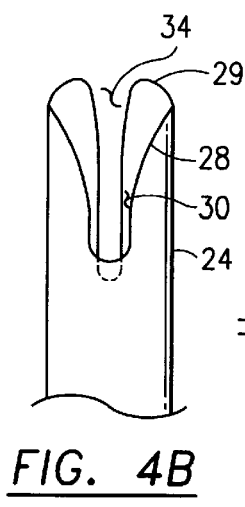
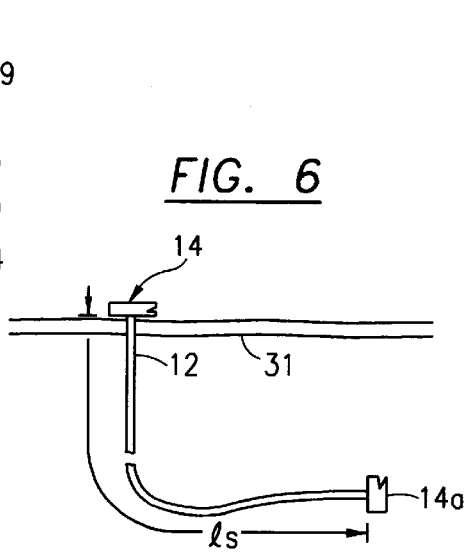
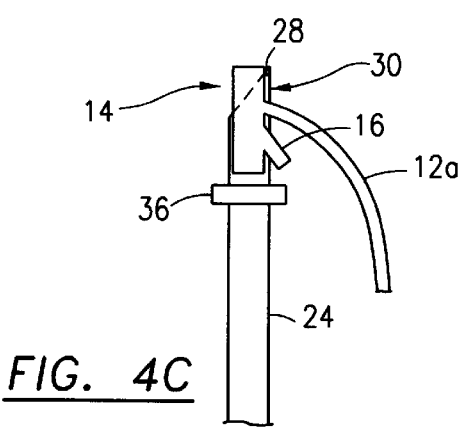
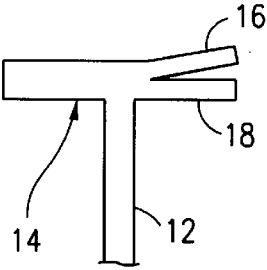
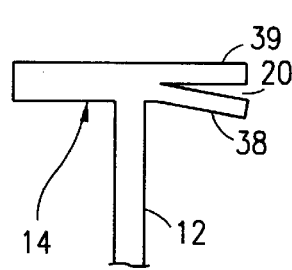
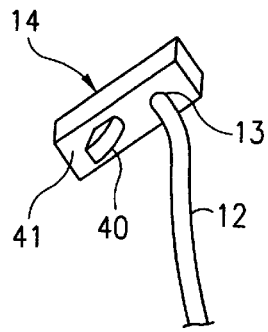
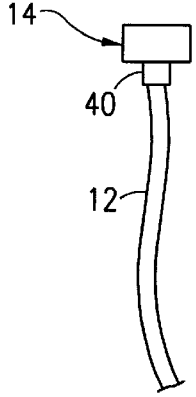
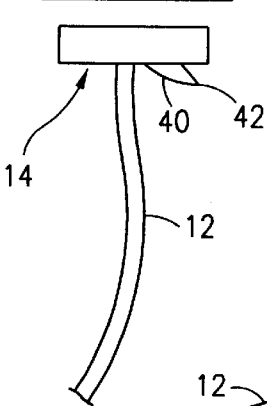
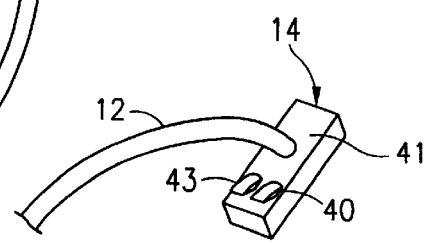

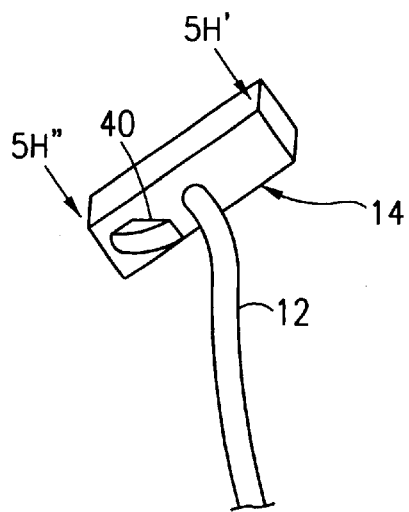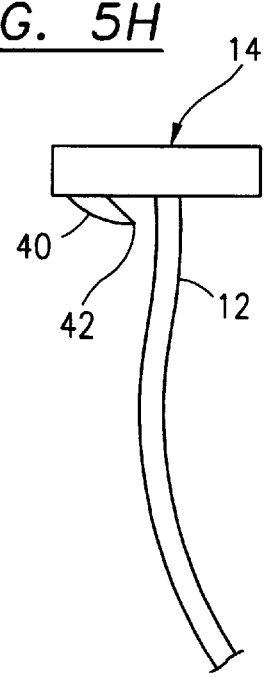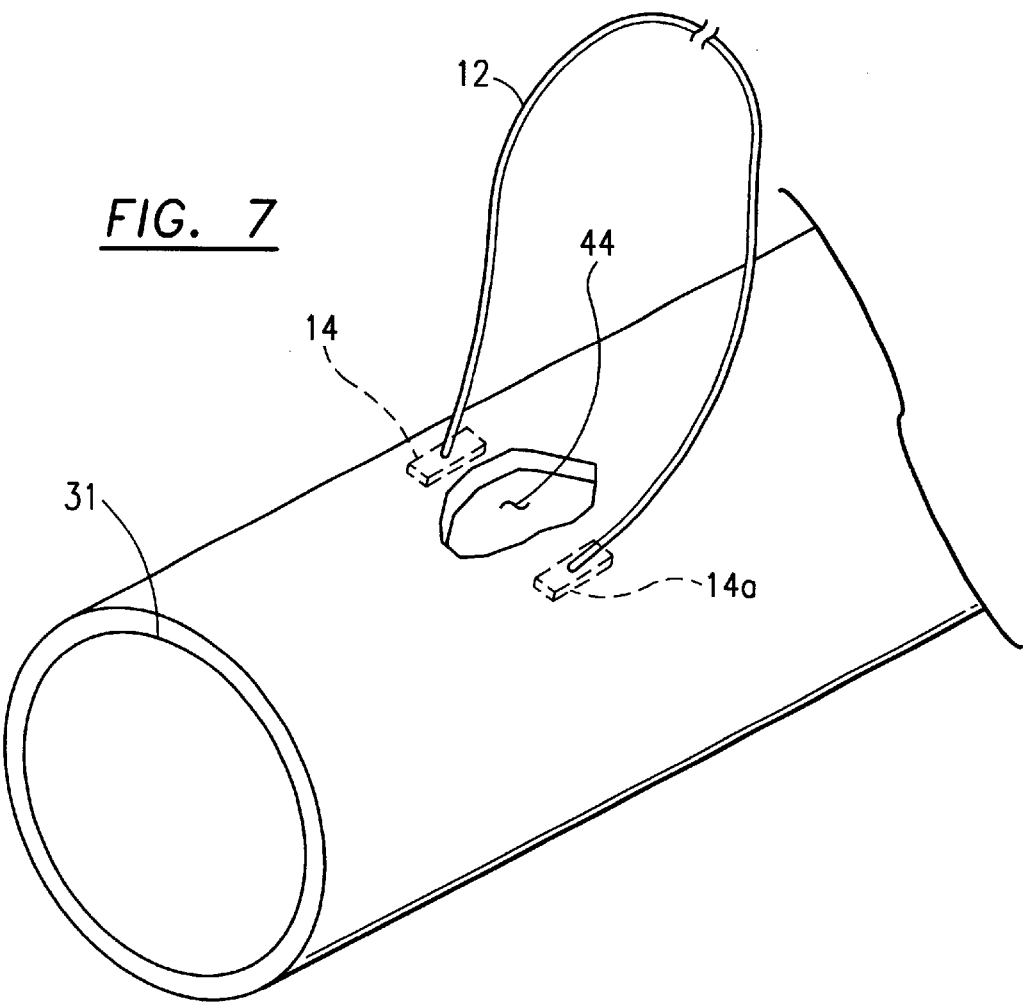

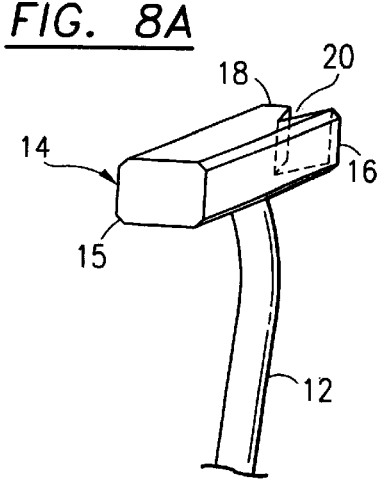 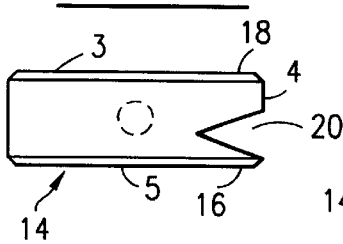 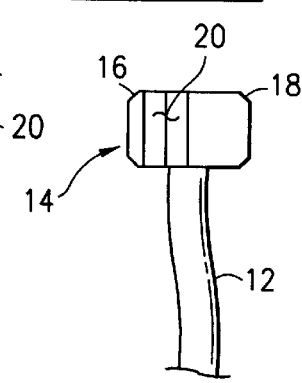
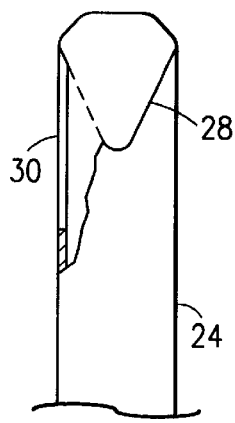 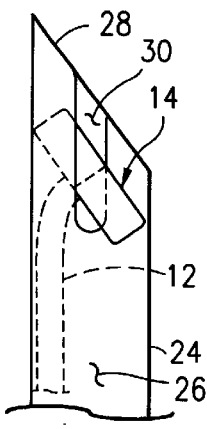 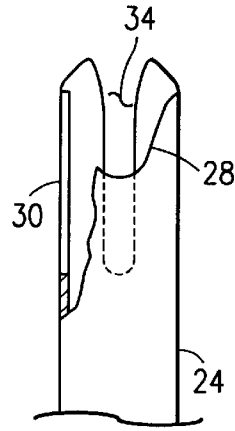 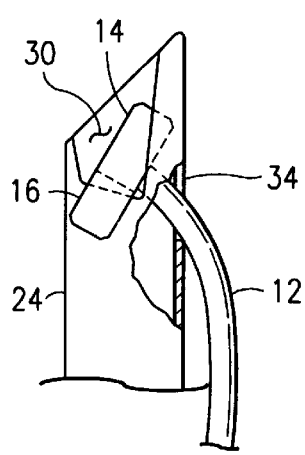
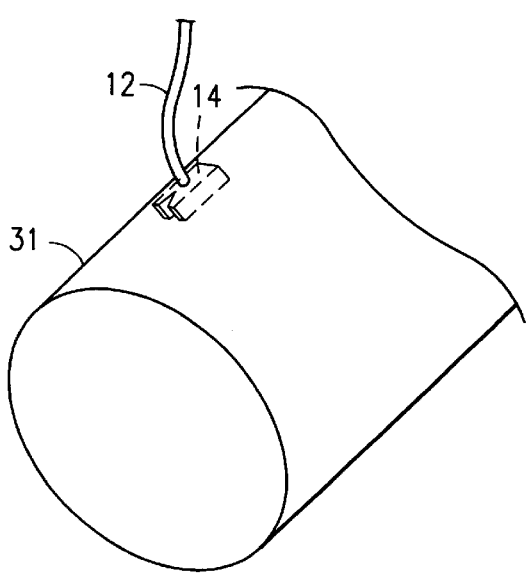 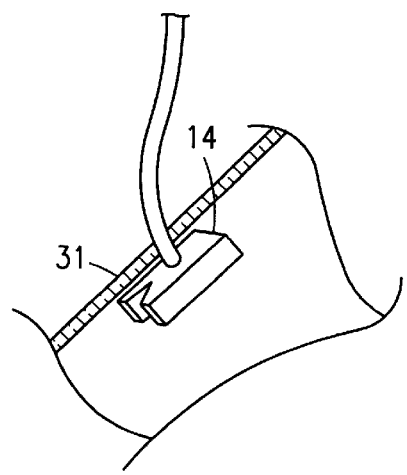

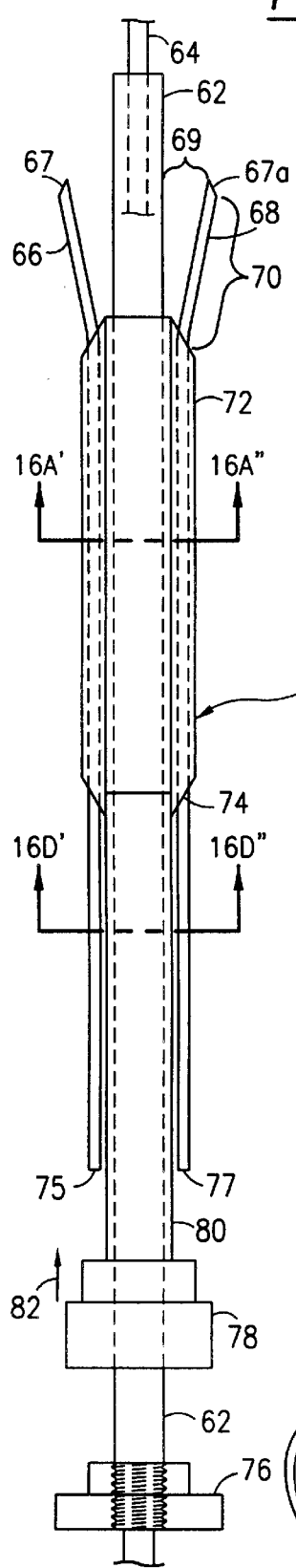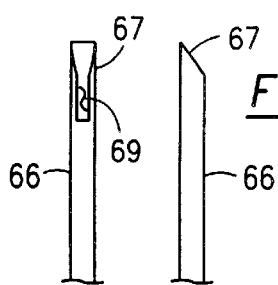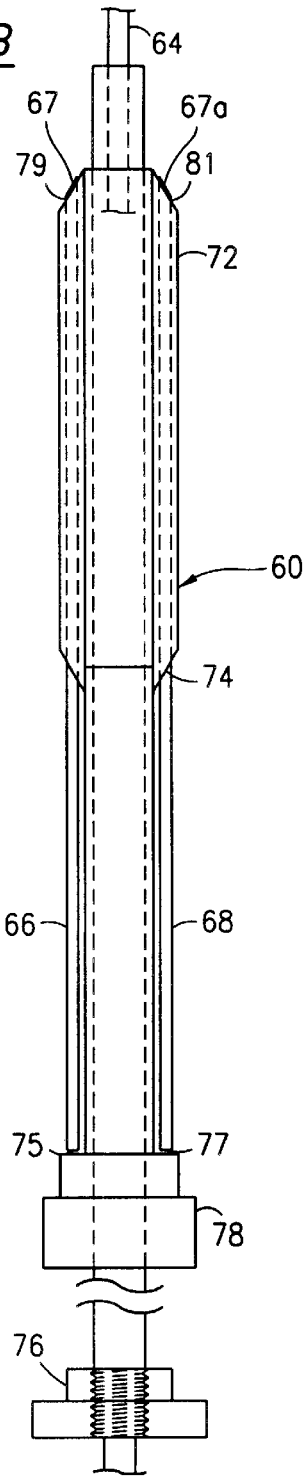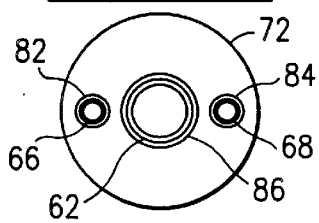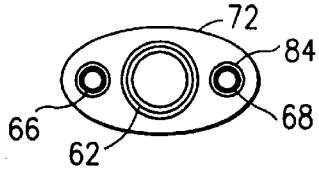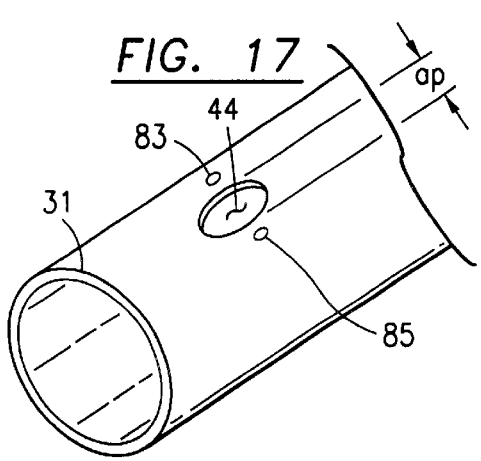

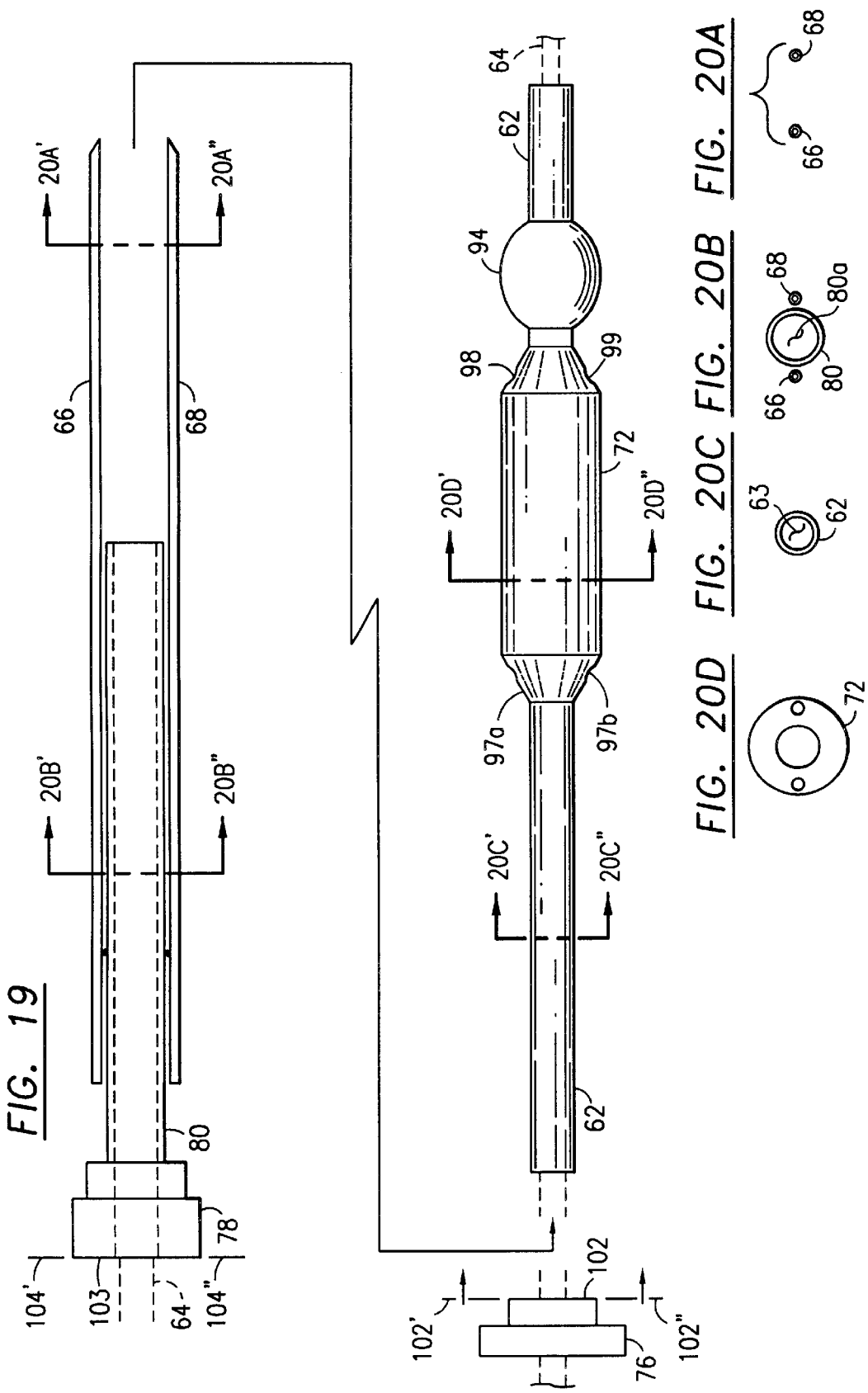

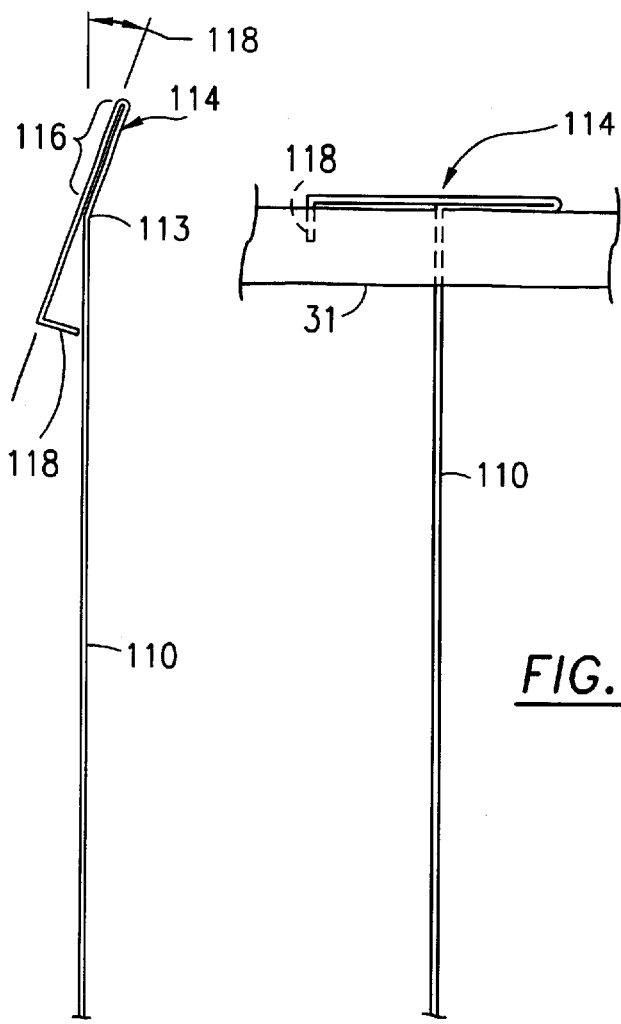
*FIG. 21A*
*FIG. 21B*
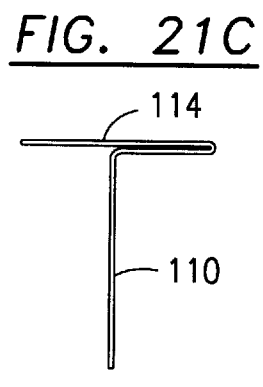
*FIG. 21C*
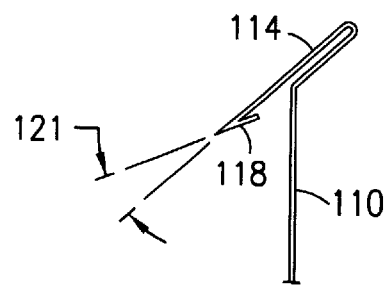
*FIG. 21D*

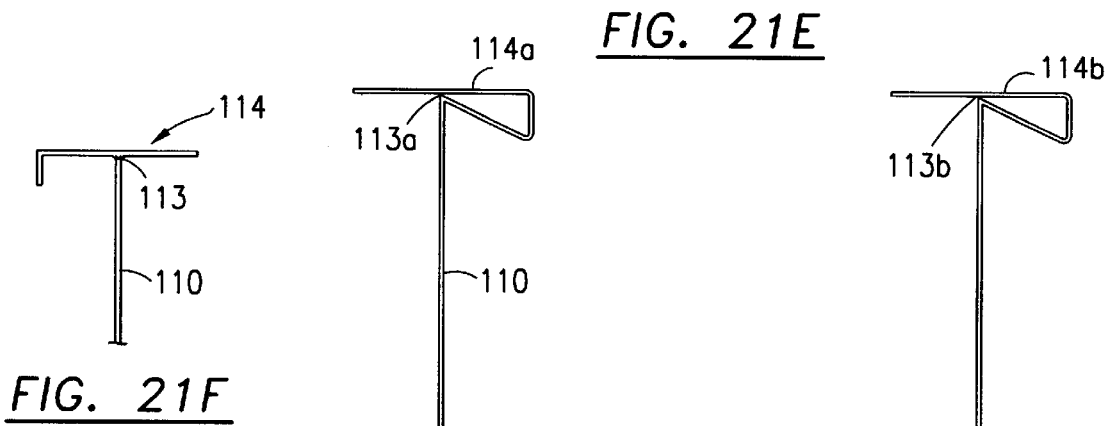
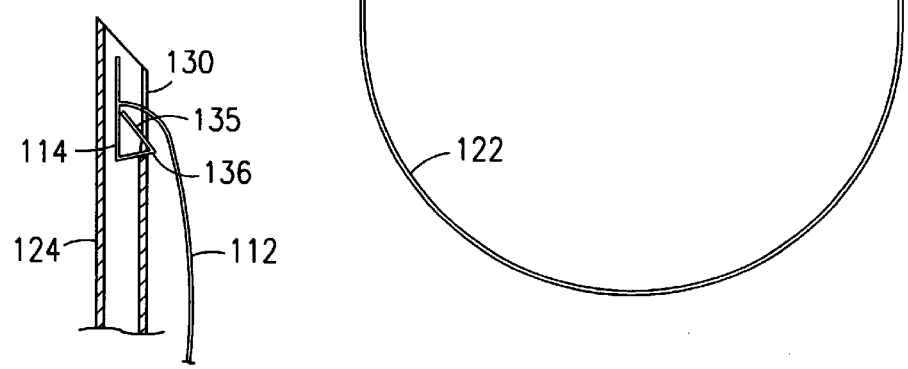
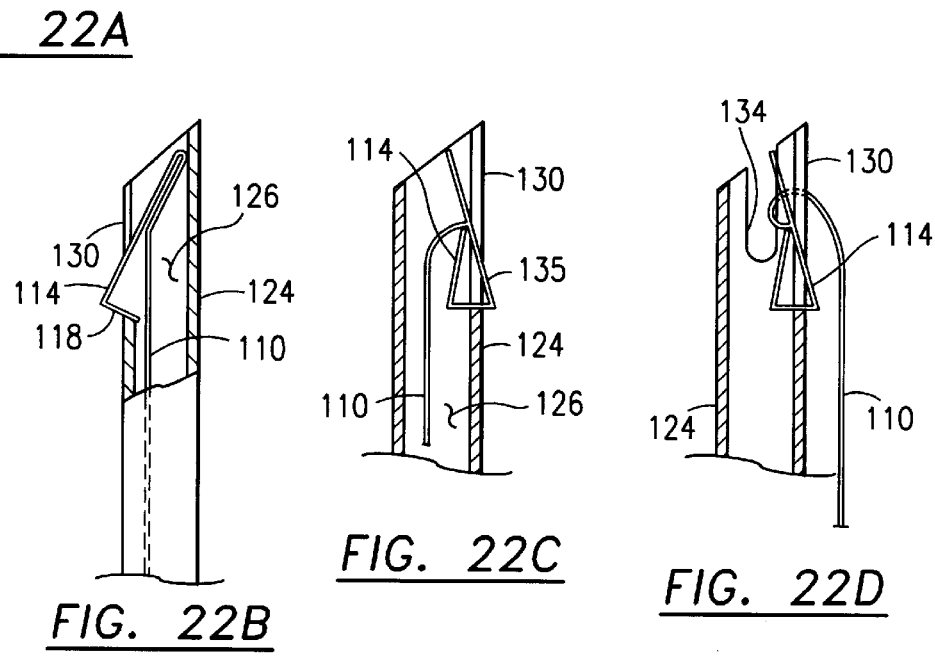

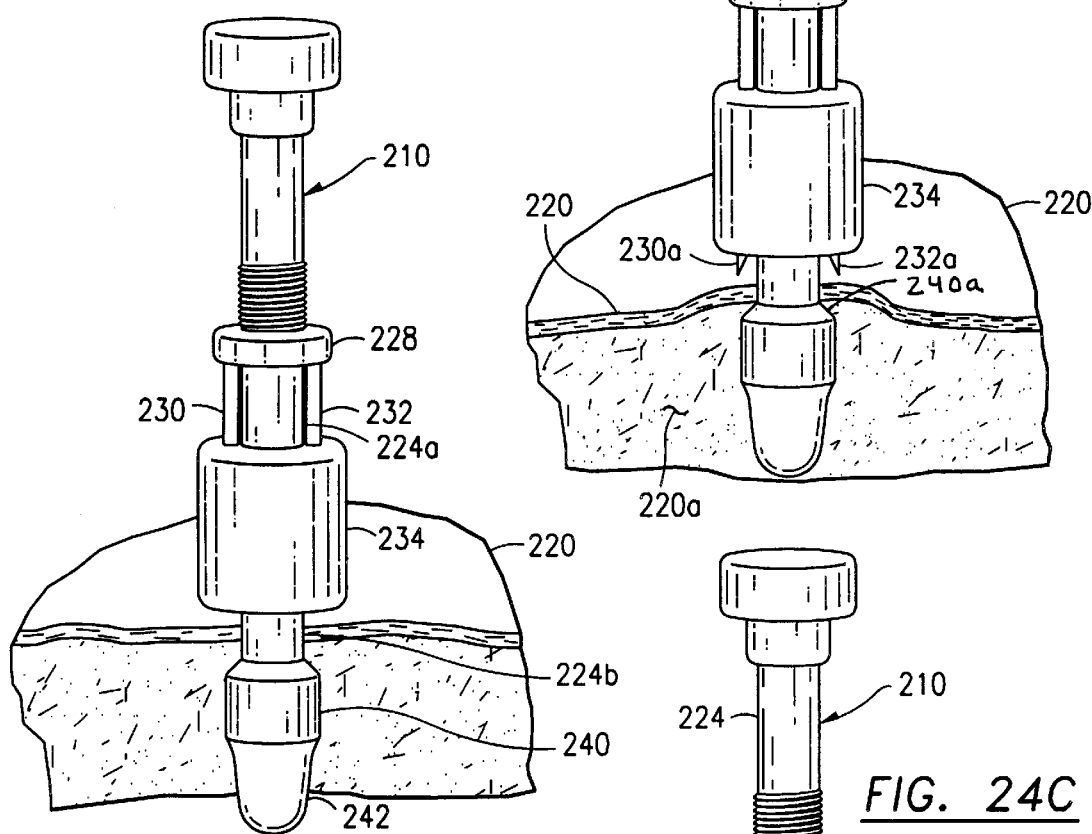

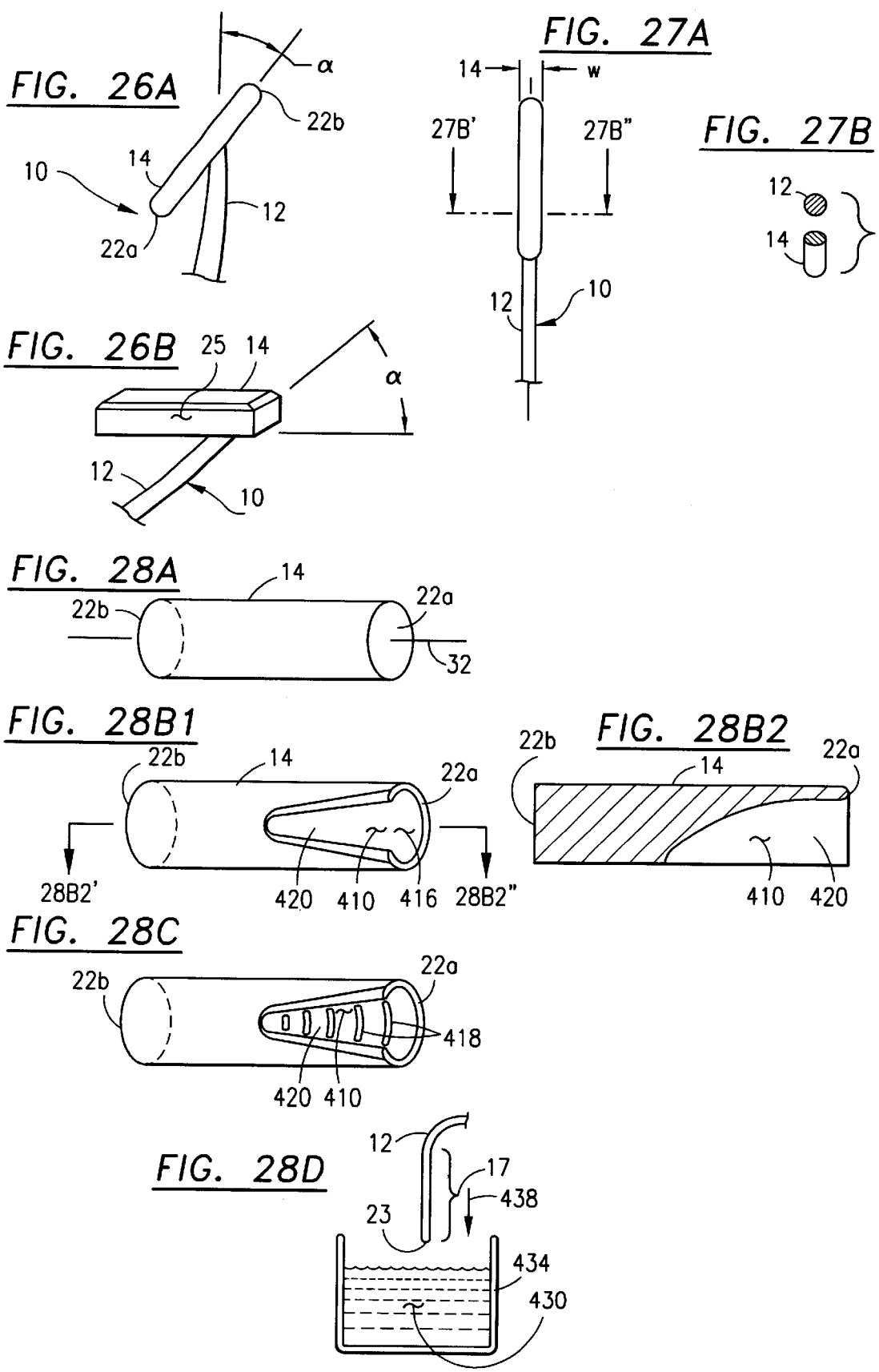

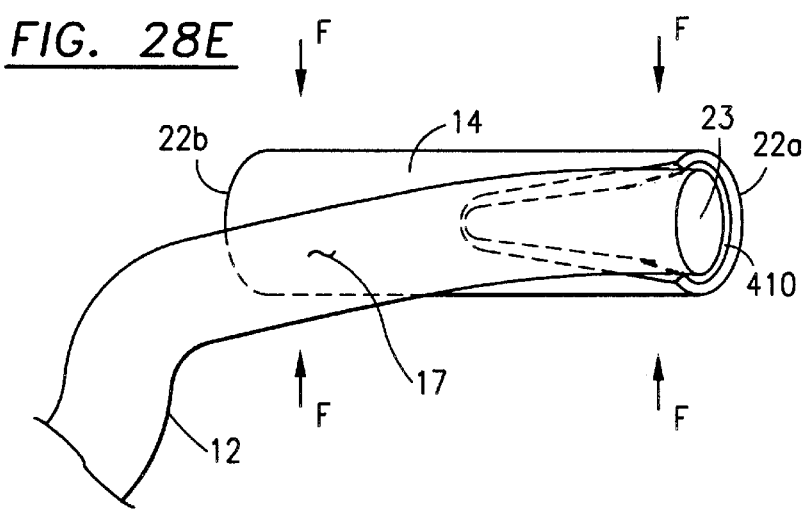
FIG. 28E
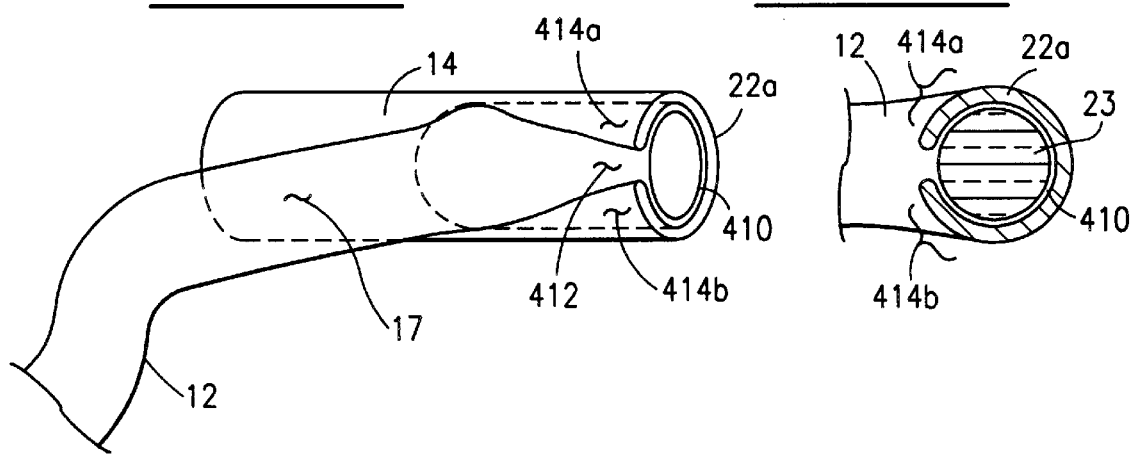
FIG. 28F1    FIG. 28F2
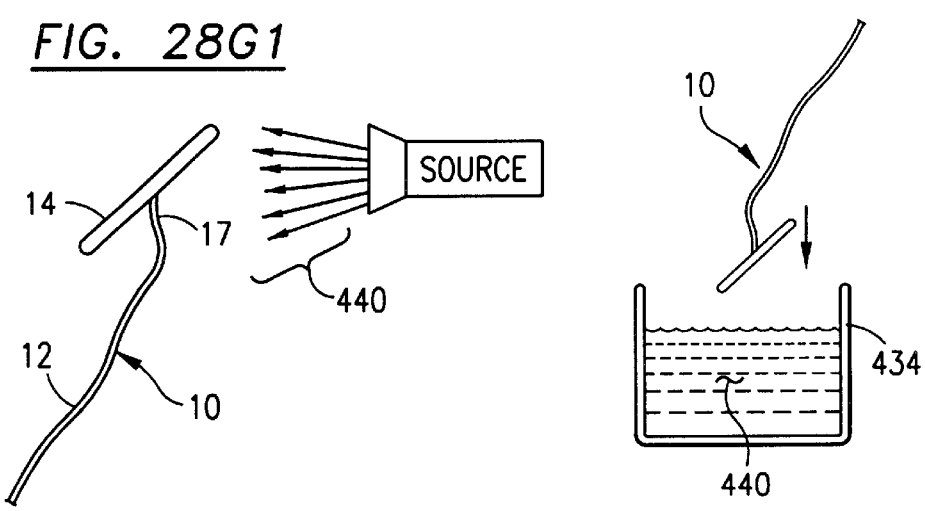
FIG. 28G1    FIG. 28G2

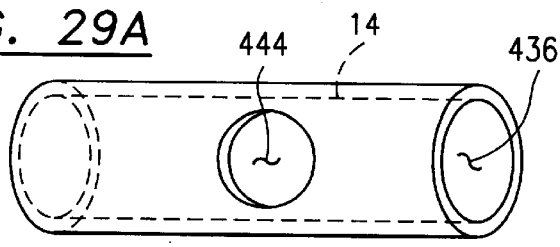
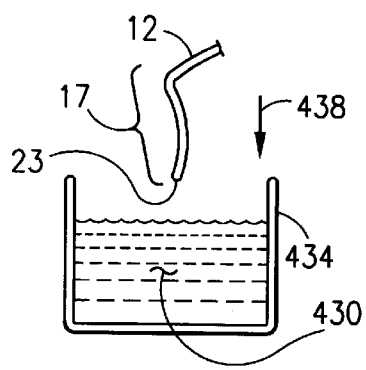
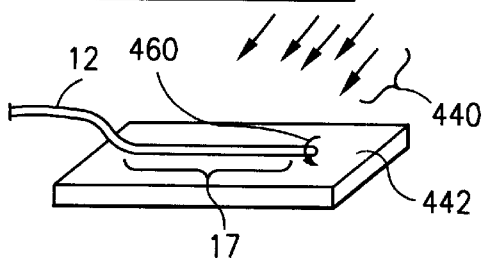
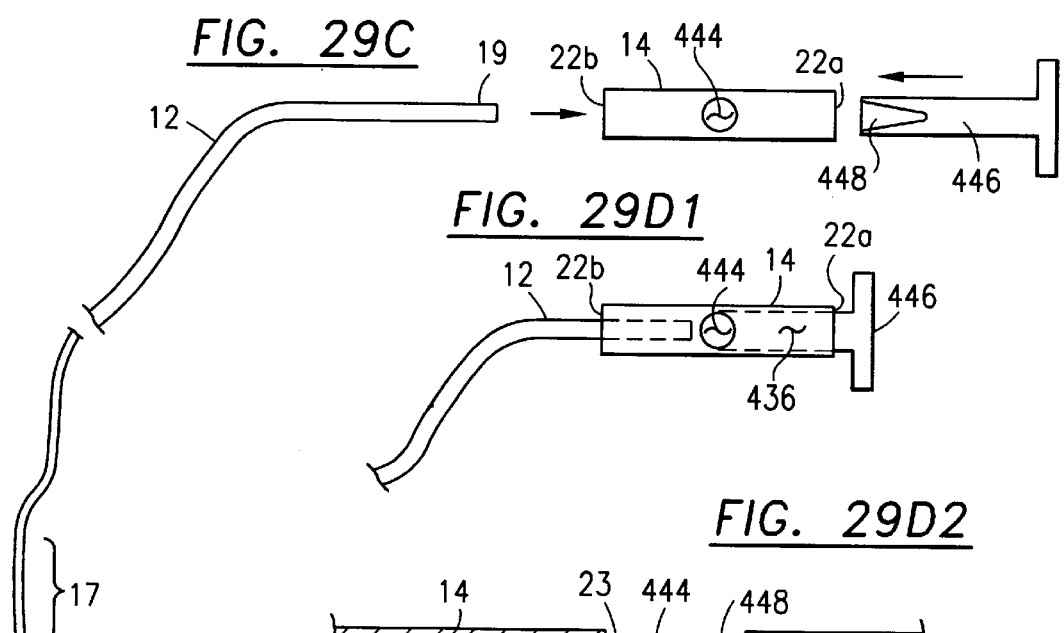

SUTURE WITH TOGGLE AND METHOD OF MANUFACTURE THEREFOR

This is a continuation-in-part patent application based upon patent application Ser. No. 09/661,024 filed Sep. 13, 2000, now U.S. Pat. No. 6,319,263 which is a continuation of patent application Ser. No. 09/413,145 filed Oct. 6, 1999 now U.S. Pat. No. 6,206,895, which is a regular patent application based upon provisional patent application Ser. No. 60/143,555 filed Jul. 13, 1999.

BACKGROUND OF THE INVENTION

In order to pass a suture through a tubular organ or other structure in a body (a human body or an animal), it is necessary to traverse the bodily structure, tissue or organ completely and encircle the area where the physician or medical practitioner wishes to place the suture. This traverse and encircle method works well in situations where easy access is available to the structure, tissue or organ and the item to be sutured is easily viewed by the physician. In limited access situations (for example, in laparoscopic surgery, cardiac surgery and vascular surgery), the traverse and encirclement by sutures is often times difficult, dangerous and at other times impossible.

As a further example, an attempt to suture a blood vessel through a small puncture wound is almost impossible. The direct suture of the arterial puncture is not possible.

The increasing utilization of minimally invasive surgical techniques has created a need for improved methods, suture systems and suture placement devices under adverse conditions of limited access and limited visibility of the suture site.

U.S. Pat. No. 5,860,990 to Nobles et al. discloses a suturing device which includes sutures attached to needle points. The needle points are press fit onto the ends of delivery arms. The delivery arms are made of memory-shape nitinol. When the memory shape metal is freed from the lumen of a needle, the needle points, at the terminal ends of the metal arms, flare out laterally beyond the lumen of the needle. The arms are then pulled proximally, causing the needle points to penetrate the vessel wall from inside out. The needle points are then captured by suture catches which are also laterally disposed outboard of the delivery system. The catches pull the needle points and draw in the sutures.

U.S. Pat. No. 5,053,046 to Janese discloses a dural sealing needle. The dural ceiling needle includes a gelatin sealing compound that swells and sits between an impact cone cavity and an impact cone protrusion. Wings spread out based upon the swelling of the gelatin seal and assist in the retention of the suture seal.

U.S. Pat. No. 4,744,364 to Kensey discloses a flexible disc-shaped body at the end of a suture thread which expands after being pushed out from the lumen of a delivery needle. In the lumen, the body is contracted or compressed.

U.S. Pat. No. 4,741,330 to Hayhurst discloses an apparatus for anchoring cartilage. The anchor is deformed in the lumen of a delivery tube, is thereafter pushed from the tube and springs laterally outward upon exiting the tube. One of the embodiments of the suture includes a flexible anchoring device which has a U-shape when loaded within the delivery needle. Hayhurst also discloses that "one end of the suture 12 may be securely attached to the anchoring device 10 during the molding or forming of the anchoring device. Preferably, the free opposite end 13 of the suture is hardened or stiffened as by impregnation with a suitable plastics material." col. 5, lines 21–26.

U.S. Pat. No. 4,705,040 to Mueller et al. discloses a suture with a T-shaped bar attached to the end of the suture. The bar is a stiff stainless steel tubing with an internal diameter of 0.025 inch and with a central hole formed in its side. The suture filament is fit within the hole and the bar heated to melt the end of the suture with the result that the resinous filament melts and draws into the form of a large central ball. When cooled and set, the ball is substantially larger than the hole, thereby creating a firm root for the filament within the bar.

U.S. Pat. No. 4,669,473 to Richards, et al., discloses a surgical fastener or suture with a t-bar formed out of a resilient polymerized resin. Richards T-shaped suture head has at least one portion of the T with a sharp point so that when the head portion is implanted in the body tissue, the head portion will attach itself securely to the tissue and will remain there despite a pulling force on the filament. The suture head is integral with the filament and the fastener is formed so that the head normally extends at a right angle to the adjoining length of filament.

U.S. Pat. No. 4,006,747 to Kronenthal, et al., discloses H-shaped fasteners constructed of a flexible and resilient biocompatible material. Each fastener has a filament with a rod-shaped head attached at either end. Kronenthal discloses an embodiment in which the heads are molded from the same material as the connecting filament. Kronenthal also discloses an alternative embodiment wherein stainless steel heads are each attached by swaging multifilament suture which enters the fastener head at the midpoint thereof with one end of the suture filament contained within one-half section of each head.

OBJECTS OF THE INVENTION

It is an object of the present invention to provide a suture which can be self secured on a bodily structure, tissue or organ with a toggle at the terminal end of the suture.

It is another object of the present invention to provide a generally T-shaped toggle which latches on an interior or inboard surface of a bodily structure, tissue and organ thereby permitting the balance of the suture to be drawn in and wherein the toggle grasps the bodily structure, tissue and organ.

It is a further object of the present invention to provide a toggle configured as a bar at the end of a suture.

It is another object of the present invention to provide a metal wire suture with a T-shaped toggle or a toggle wire element attached to the terminal end of a suture wire.

It is a further object of the present invention to provide a suture thread and a toggle wherein the toggle includes a protruding leg or tab which is utilized by a needle delivery system to insert the suture toggle into the bodily structure, tissue or organ.

It is a further object of the present invention to provide a self-securing suture toggle wherein the suture thread and toggle are attached to form an acute angle.

It is a further object of the present invention to provide a method of manufacture to produce self-securing suture toggles with toggles attached at an acute angle to the suture thread.

It is a further object of the present invention to provide a suture toggle in which an end segment of the suture thread is stiffened.

It is a further object of the present invention to provide a suture delivery system including a slotted needle, within which is seated the leg or tab of the toggle, which assists in the process of inserting the suture toggle into the bodily structure, tissue or organ.

It is another object of the present invention to provide a self securing suture with a toggle which can be used for minimally invasive surgical techniques.

It is a further object of the present invention to provide a suture delivery system and toggle sutures utilized in laparoscopic procedures.

SUMMARY OF THE INVENTION

The self securing suture includes a suture having a stiff end segment at a terminal end and a toggle disposed on the terminal end such that the stiff end segment and toggle define an acute angle between 25 degrees and 65 degrees. The toggle may include a metal body toggle or a biocompatible plastic body toggle. An embodiment of the suture toggle includes a biocompatible coating of the toggle and stiff end segment. In one embodiment, a portion of the stiffened end segment is swaged onto the toggle in a closed channel. In another embodiment, a portion of the stiffened end segment is swaged onto the toggle in a closed cutout. The present invention also includes methods for producing suture toggles. One method includes creating a partial channel on a toggle, stiffening an end segment of a suture thread, positioning a portion of the stiffened end segment in the partial channel, and swaging the toggle channel closed about the portion of the stiffened end segment lying therein. The method may include roughening the channel surface prior to swaging. The method may also include aligning the stiffened end segment and toggle such that the two define an acute angle. In addition, the method may also include the step of coating the toggle and stiffened suture thread with a biocompatible polymer after the swaging step. An alternative method of manufacture for producing the suture toggle includes the steps of creating a longitudinal passage through a toggle, forming a lateral hole through the toggle and into the passage, stiffening an end segment of a suture thread, placing the suture thread in the passage and through the hole of the toggle such that a portion of the stiffened end segment lies in the passage and protrudes from the hole, swaging the toggle closed about the captured stiffened end segment, and coating the toggle and the portion of the stiffened end segment of the suture thread with a biocompatible material. In yet another method of manufacture for producing a suture toggle, a mold is provided defining a toggle-shaped cavity and a suture thread-shaped cavity communicating therewith. The mold may also include a protruding member-shaped cavity communicating with the toggle cavity. The method includes stiffening a suture thread end segment, positioning the suture thread end segment within the suture thread cavity of the mold, and molding a toggle onto the positioned suture thread end segment at an acute angle utilizing the mold. This method may be utilized such that the positioning step occurs prior to the stiffening step, and the stiffening step occurs substantially concurrently with the molding step. The stiffening of the suture thread end segment may be accomplished by cold dipping same into a polymer or spraying the end segment with a biocompatible acrylic.

BRIEF DESCRIPTION OF THE DRAWINGS

Further objects and advantages of the present invention can be found in the detailed description of the preferred embodiments when taken in conjunction with the accompanying drawings in which:

FIGS. 1A and 1B diagrammatically illustrate a suture with a toggle;

FIGS. 2A and 2B diagrammatically illustrate a suture delivery needle with and without the suture toggle;

FIGS. 3A, 3B, 3C, 3D and 3E diagrammatically illustrate the insertion and deployment of the suture toggle and, more particularly, FIG. 3E generally diagrammatically illustrates the size relationship between the suture toggle and a typical large artery in a human body;

FIGS. 4A, 4B and 4C diagrammatically illustrate a suture delivery system needle, a suture toggle and a modified delivery system;

FIGS. 5A–5F diagrammatically illustrate various protruding legs, tabs and other elements protruding from the toggle which assist in deployment of the suture toggle in the bodily structure;

FIGS. 5G and 5H diagrammatically illustrate various suture toggles with depending tabs;

FIG. 6 diagrammatically illustrates a suture having two terminal ends and two toggles;

FIG. 7 diagrammatically illustrates a suture toggle with two toggles at both terminal ends of a suture thread, deployed about an arterial puncture site;

FIGS. 8A–8C diagrammatically illustrate other suture toggles;

FIGS. 9A–9D diagrammatically illustrate a suture delivery system with and without a suture toggle;

FIGS. 10A and 10B diagrammatically illustrate the deployment of the suture toggle illustrated in FIG. 8A;

FIGS. 14A and 14B diagrammatically illustrate one delivery system for the suture toggle utilized in conjunction with minimally invasive surgery;

FIGS. 15A and 15B diagrammatically illustrate front and side views of the suture delivery needle;

FIGS. 16A, 16B and 16C diagrammatically illustrate various configurations of the needle retention body or structure;

FIG. 16D is a cross-sectional view of the delivery system from the perspective of section line 16D'–16D" in FIG. 14A;

FIG. 17 diagrammatically illustrates an arterial puncture site in a large artery in a human;

FIG. 19 diagrammatically illustrates an exploded view of the suture delivery system shown in FIG. 18;

FIGS. 20A, 20B, 20C and 20D diagrammatically illustrate cross sectional views of the delivery system shown in FIG. 19 from the perspective of the corresponding section lines in FIG. 19;

FIGS. 21A–21F diagrammatically illustrate various configurations of wire sutures and wire toggle elements;

FIGS. 22A–22D diagrammatically illustrate needle delivery systems for the wire suture toggles;

FIGS. 24A–24C diagrammatically illustrate major operational steps to deploy suture toggles during laparoscopic surgery with the delivery system shown in FIG. 23A;

FIGS. 26A and 26B diagrammatically illustrate a suture toggle with its toggle and suture thread defining an acute angle therebetween;

FIG. 27A diagrammatically illustrates a suture toggle with its toggle angularly mounted on its suture thread;

FIG. 27B diagrammatically illustrates a cross-sectional view of the suture toggle from the perspective of section line 27B'–27B" in FIG. 27A;

FIGS. 28A, 28B1, 28B2, 28C, 28D, 28E, 28F1, 28F2, 28G1 and 28G2 diagrammatically illustrate the steps in one method of manufacturing a suture toggle;

FIGS. 29A, 29B1, 29B2, 29C, 29D1 and 29D2 diagrammatically illustrate the steps in an alternative method of manufacturing a suture toggle;

DETAILED DESCRIPTION OF THE PREFERRED EMBODIMENTS

The present invention relates to self securing sutures, that is, sutures having toggles at the suture's terminal end, and various suture delivery systems.

Figure 18:
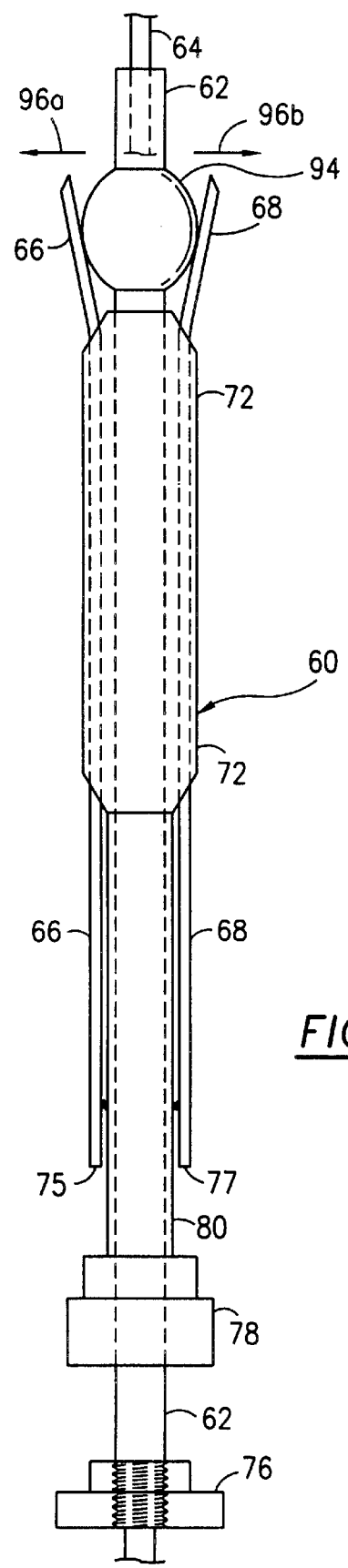
FIG. 18 diagrammatically illustrates another type of suture delivery system.
Figure 23A:
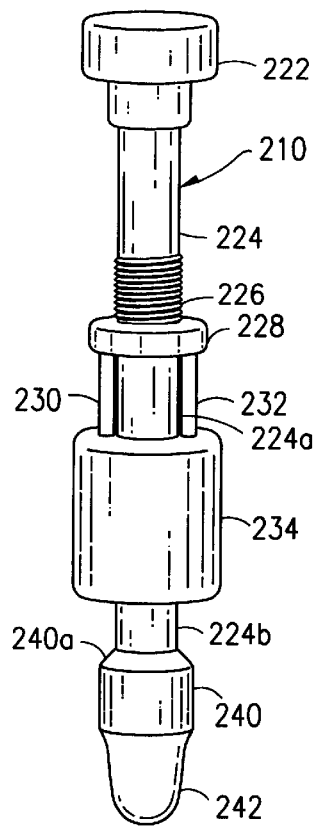
FIGS. 23A–23C diagrammatically illustrate a laparoscopic device for the suture toggle delivery system and FIG. 23D is a cross-sectional view of a suture wire capture system (similar capture systems may be used with suture threads on the delivery systems in FIGS. 14A and 18)

FIGS. 1A, 1B, 2A and 2B diagrammatically illustrate sutures having toggles at the terminal end and a needle delivery system used in conjunction with the suture toggles. FIGS. 14A and 18 diagrammatically illustrate simple delivery systems for the suture toggles. FIGS. 21A, B, C, D, E and F show wire suture toggles and FIG. 23A shows a delivery system for laparoscopic surgery or other type of surgery wherein the surgeon seeks to suture fascia.

General Principles

By utilizing the toggle principle, it is possible to enter the bodily structure, tissue or organ and fix one end of a suture to the structure or tissue without encircling the area. If two separate toggle sutures are fixated in this fashion, it becomes possible to tie those sutures with ease without the need for blind encirclement of the area in question. The increasing utilization of minimally invasive surgical techniques and arterial puncture site repair has created a need for improved methods of suture placement under adverse conditions of visibility and access.

The toggle principal lends itself well to the placement and fixation of sutures, ligaments, etc. In this approach, a suture or wire or other flexible attachment or closure device is passed through or into the tissue in a closed state. The "closed state" refers to the suture toggle deployed in the needle. Upon applying tension after the toggle leaves the needle tip, the toggle is positioned so that it cannot retrace the path through which it was applied or inserted by virtue of the fact that its shape and position will no longer allow egress from the bodily structure or tissue. Structures such as sutures or ligaments attached to the toggle are thereby fixed. One general embodiment of this invention consists of a T-shaped attachment to the end of a suture of either the same or different biocompatible material. The T bar is stiffer than the suture line, thread or wire and offers significant resistance to extraction from the bodily structure once deployed. The suture toggle design in fine wire allows the insertion of the toggle, but restricts the egress from the tubular structure. With respect to wire sutures, provision is made for the applying or delivery device to secure both wires together and close the defect by shortening the wire by the simple, but effective, expedient means of twisting the instrument and its contained wires to secure them together. Provision is made to score the wires at the appropriate location so that the wires divide or separate upon twisting with a small, but secure, stub of twisted wire. In the alternative, a twisting and cutting instrument can be slid down the two opposing wires after the applicator is removed and the wires retained. This instrument would permit twisting and subsequent cutting of the wires in a blind procedure.

Basic Details of Operation

The applying device or delivery system consists of a small hollow core needle which allows it to be passed over a guide wire which has been retained at the puncture site. The delivery system contains two small hollow needles in opposition at just the right distance on either side of the guide wire and, thus, the puncture site. In another iteration, the needle can be solid with hollow small toggle suture ends fitted over the needle rather than through them. In the first design, the needles are designed to contain the toggles and the wire or sutures. When the instrument is slid over the guide wire and through the skin incision site of puncture it is advanced until it is against the vessel or structure sought to be closed by a suture. In the case of a vein or artery, a "flashback" tube can be utilized in advance of the needles to demonstrate that the instrument is in the proper position. In addition, the length and design of the "flashback tube" is such that it protects the far wall of the structure, preventing toggling of two walls simultaneously. The restricted length of the hollow needles also protects opposite walls of the artery or vein. A slide moves the two needles distally and then advances the needles through the vessel or structure wall until the toggles are deposited in the blood vessel with their trailing suture or wire leading from the vessel. The hollow needle also acts as a flashback tube bilaterally. The shape of the toggle, as designed, prevents egress from the vessel and traction on the wire or suture "sets" the T of the toggle flush against or in the structure wall. The suture is then tied or the wire twisted as appropriate.

Different toggle designs are provided as shown in the accompanying drawings. In this fashion, puncture wounds or other defects may be easily closed utilizing simple and inexpensive devices. The cost of complicated closure devices has been a deterrent to the universal acceptance of these previous devices. The utilization of a simple, inexpensive disposable device should remove many of the impediments for universal usage. The concept of toggling sutures for closure is new, safe and simple to use.

In one of the embodiments presented here, fine, partially annealed wire sutures are utilized to simplify the process by permitting fastening by simple twisting of the wires by the instrument, instead of having to resort to complex methods of tying. Scoring the wires at the appropriate distance allows them to break with twisting at a predetermined location leaving only a small wire stump on top of the structure.

Any biocompatible material for the suture toggle may be used such as stainless steel wire, nylon sutures, or other synthetic biocompatible material. The methods of tying the sutures may vary with the materials used, but the toggling principle remains the same.

FIGS. 1A and 1B diagrammatically illustrate a suture 10 having a suture thread or suture body 12, a terminal end 13 and a toggle 14. FIG. 1B shows a side view of suture toggle system 10. In the illustrated embodiment, toggle 14 is generally a solid rectangular shape having a length 1, a width w (FIG. 1B) and a depth d. The width w of the toggle 14 is substantially similar to the outside diameter of the suture thread 12 as shown in FIG. 1B. Toggle 14 has chamfered ends and edges, one of which is chamfer edge 15. This chamfer reduces sharp edges. Further, toggle 14 includes an extending leg 16 protruding outboard away from terminal end 13 of suture 12. Extending leg 16 defines, in combination with toggle body element 18, an open catch mouth 20 leading to a narrower throat 21. Mouth 20 has a gap size large enough to be captured by a slot in the delivery needle discussed later. Leg 16 protrudes in a direction opposite the attachment of suture 12 to toggle 14.

FIGS. 2A and 2B diagrammatically show a suture delivery system 8 which includes needle 24 having a lumen 26, a piercing terminal end 28 and an open ended slot 30. Open ended slot 30, sometimes called a needle toggle slot herein, is open at the piercing end segment 28 of needle 24. In the illustrated embodiment, piercing terminal end segment 28 (typically a sharp edge) of needle 24 is angularly disposed with respect to the axial center line of needle 24.

Suture toggle system 10 is shown as disposed in lumen 26 of needle 24 in FIG. 2B. Toggle 14, and particularly protruding leg 16, is adapted to seat within slot 30 of needle 24.

FIGS. 3A–3D diagrammatically illustrate basic operational characteristics of suture toggle system 10. Similar numerals designate similar items throughout all the drawings. In FIG. 3A, suture delivery system 8, consisting of needle 24 loaded with suture 12 and toggle 14, approaches a bodily structure, tissue or organ wall 31. As an example throughout the drawings (excepting drawings FIGS. 24A–24C), reference will be made to arterial wall 31. However, any type of bodily structure, tissue or organ may be sutured using the suture toggle system 10 discussed herein. Wall 31 is representative of other bodily structures tissues and organs. Delivery system 8 approaches arterial wall 31 as shown by arrow 33. Piercing end 28 of needle 24 ultimately pierces and enters arterial wall 31.

FIG. 3B diagrammatically shows that needle 24 has fully entered and passed through arterial wall 31. At this point in time, blood flow is noted by a "flash" from the lumen 26 of needle 24. Other "flash back" systems may be utilized. See central tube 62 in FIG. 14A. This flash of blood provides a visual indication to the physician that the needle 24 has fully penetrated into the lumen of the artery or other structure.

In FIG. 3C, the physician is withdrawing needle 24 and protruding leg 16 of toggle 14 is caught on the inboard surface of arterial wall 31. In FIG. 3D, needle 24 is withdrawn from arterial wall 31 and toggle 14 and suture 12 is self secured in artery wall 31.

FIG. 3E diagrammatically illustrates the general proportional size relationship between artery wall 31, the artery in general, toggle 14 and suture 12. To further illustrate one proposed embodiment of the suture toggle, the following Exemplary Dimensional Table is provided.

| Exemplary Dimensional Table | |
| --- | --- |
| toggle head length | 0.10–0.12 mm |
| toggle head depth | 0.020 mm |
| OD suture | 3/0 nylon |
| suture length | 18 inches |
| toggle head width | 0.10–0.012 mm |
| gap | 0.008 mm or more |
| typical delivery needle | 0.028 mm OD |
| | 0.023 mm ID |
| | 21 gauge |
| large artery size | about 7 mm ID |

FIG. 4A diagrammatically illustrates toggle 14 and suture thread 12 disposed in needle 24. Protruding leg 16 is also disposed in slot 30. However, suture thread 12A is disposed outside of needle lumen 26. This is accomplished by providing a secondary slot 34 within which passes suture thread A. Secondary slot 34 is sometimes referred to herein as a suture slot in the needle.

FIG. 4B diagrammatically shows open ended suture slot 34 at terminal end 29 of needle 24. Terminal end 29 of needle 24 is part of piercing terminal end 28. In the illustrated embodiment, suture slot 34 is opposite toggle slot 30 which retains, in a loaded mode, protruding leg 16 of toggle 14. The position of the suture slot relative to the toggle slot varies dependent upon the position of the protruding leg, tab, wire element or loop on the suture toggle.

FIG. 4C diagrammatically shows needle 24 within which is loaded toggle 14. Protruding leg 16 protrudes towards suture thread 12A. In this illustrated embodiment, slot 30 also operates as a suture slot. In addition, needle 24 includes rib 36 which enables the suture needle to be inserted into the blood vessel 31 by a pushing in action.

FIGS. 5A through 5H diagrammatically illustrate various modifications of toggle 14. FIG. 5A diagrammatically illustrates toggle 14 having a protruding leg 16 which protrudes outboard from the toggle opposite suture thread 12. Particularly, toggle 14 is a toggle bar. As used herein, the term "toggle" refers to apiece or a device for holding or securing suture thread 12. The term "toggle" also encompasses the concept that it is a cross piece attached to the end of suture thread 12 in order to prevent slipping or removal of the suture. The following Bar Shape Table provides some illustrative examples of the geometric shape of the toggle bar.

| Bar Shape Table |
| --- |
| a straight piece of suture material which is longer than it is wide |
| rectangular |
| oblong |
| elliptical |
| an elongated cylinder |

As used herein, the term "bar" refers to a straight piece which is longer than it is wide. As shown in FIG. 5A, leg 16 is formed from a partially separated segment of toggle bar 14. Remaining segment 18 continues to form part of the toggle bar basic shape.

FIG. 5B shows a depending protruding leg 38 which protrudes inboard toward suture thread 12. Leg 38 is cut away or formed from toggle bar segment 39. Leg 38 is retained by and captured within open ended toggle slot 30 of needle 24. Gap 20 between leg 38 and toggle remainder section 39 is one of the important features.

FIG. 5C diagrammatically illustrates toggle 14 including a tab 40 depending from inboard surface 41 of toggle 14. Inboard surface 41 is integral with or attached to suture terminal end 13. Surface 41 is inboard with respect to suture thread 12.

FIG. 5D diagrammatically shows tab 40 depending toward suture thread 12. FIG. 5D shows tab 40 consisting of either a solid triangular body, a finger or a conical body. The width of tab 40 is smaller than toggle 14. Protruding tab 40 has a raised terminal edge 42, see FIG. 5E, which faces away from suture thread 12. Tab 40 coacts with open ended slot 30 of suture delivery needle 24 (see for example FIG. 4B). The tab fits in toggle slot 30. In a different embodiment, suture slot may be placed 90 degrees from toggle slot 30 (see FIG. 9C) to provide clearance of the tab from the thread during withdrawal of needle 24.

FIG. 5F diagrammatically illustrates toggle 14 carrying two tabs 40, 43 depending from inboard surface 41 of suture tab 14.

FIG. 5G diagrammatically shows tab 40 as a solid triangular body. Toggle 14 is also a solid rectangular body without chamfered edges.

FIG. 5H diagrammatically illustrates toggle 14 from the perspective of section line 5H'–5H" in FIG. 5G. Tab 40 has a raised terminal edge 42 which faces towards suture thread 14. Accordingly, the tab can either face away from suture thread 12 as in FIG. 5E or towards suture thread 12 as in FIG. 5H.

FIG. 6 diagrammatically shows toggles 14 and 14a disposed at opposite terminal ends of suture thread 12. Suture thread 12 has a length ls which is, in one embodiment, about 16–18 inches.

FIG. 6 also shows that toggle 14 has been deployed beneath body layer 31.

FIG. 7 diagrammatically shows deployed toggles 14 and 14a on blood vessel wall 31. The toggles are deployed beneath arterial wall 31. Arterial wall 31 is illustrated as having arterial puncture site 44. Toggles tabs 14, 14a are deployed on either side of puncture side 44. Suture thread 12 connects toggles 14, 14a. In operation, the surgeon or physician ties off suture thread 12 thereby closing arterial puncture site 44.

FIGS. 8A, 8B and 8C diagrammatically illustrate toggle 14 with a protruding leg 16 along one side. Particularly, FIG. 8A diagrammatically shows toggle 14 as a toggle bar with chamfers along its side edges. One of the chamfers is identified as chamfer 15. A protruding leg 16 is formed by partly separating toggle 14 from remaining toggle segment 18. This creates an open mouth 20 which is disposed in the toggle slot in needle 30. See FIG. 2A.

FIG. 8B shows a top view of toggle 14 and clearly shows that protruding and extending leg 16 is formed by partially separating leg 16 from the remaining toggle body portion 18. The generally solid body rectangular toggle bar 14 has sides 2, 3, 4 and 5 which are generally in parallel planes with respect to the axial centerline of suture thread 12 if the thread were laid out straight. Items protruding from toggle bar walls 2, 3, 4, 5 are normal (perpendicular) to the suture thread.

FIG. 8C shows a toggle end view and toggle mouth 20.

FIGS. 9A–9D show needle 24 with and without a retained toggle suture. FIG. 9A shows toggle slot 30 in needle 24 located approximately midway along piercing terminal edge 28 of needle 24. The toggle slot can be re-positioned dependent upon the size of the suture, the leg or tab, and the item to be sutured. FIG. 9B also shows toggle slot 30 of needle 24 approximately midway along needle piercing edge 28. FIG. 9B also shows toggle 14 deployed in toggle slot 30. Suture thread 12 runs or passes through the lumen 26 of needle 24.

In FIG. 9B, slot 30 retains protruding leg 16 which protrudes from side edge 5 of the toggle bar. The side edge protruding leg 16 is shown in FIGS. 8A–8C. Leg 16 protrudes normal or perpendicular to suture thread 12.

FIG. 9C shows needle 24 having toggle slot 30 and suture thread slot 34. Suture thread slot 34 is formed or created approximately 90 degrees from toggle slot 30.

FIG. 9D shows toggle 14 with a side end protruding leg 16 wherein suture thread 12 runs through suture slot 34 of needle 24.

FIG. 10A shows toggle 14 deployed in arterial wall 31.

FIG. 10B is a detailed view showing toggle 14 deployed on an inboard surface of arterial wall 31. Currently, it is believed that the toggle bar with a leg or tab protruding from bar side 2, 3, 4 and 5 is preferable.

FIG. 8B shows toggle bar 14 with side surfaces 2, 3, 4 and 5. It is currently believed that a tab or leg protruding from one of the side surfaces is better suited than an outboard extending tab or leg (see FIG. 5A) or a depending tab or leg (see FIG. 5B). The depending leg or the depending tab may injure an arterial 31 in certain situations. When toggle anchoring is required, the depending leg or wire is preferred. An upstanding or outboard tab or leg may impede blood flow. However, in some applications, these tab-leg configurations may be beneficial if they achieve better attachment by the suture toggle on the body structure, tissue or organ. A side leg or tab is currently thought to be better than an outboard leg or tab (see outboard leg 16 in FIG. 1A) because an outboard protruding leg or tab may further complicate and impede blood flow or fluid flow through the bodily structure, tissue or organ, particularly if the structure is an artery or a vein.

Figure 11A:
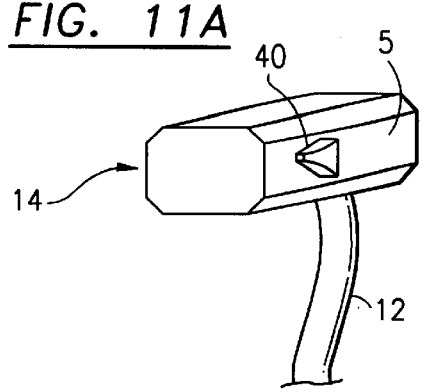
FIGS. 11A, 11B and 11C diagrammatically illustrate other types of tabs protruding from toggles.

FIG. 11A diagrammatically shows toggle 14 having a protruding tab 40 protruding from side surface 5 of the toggle bar.

Figure 11B:
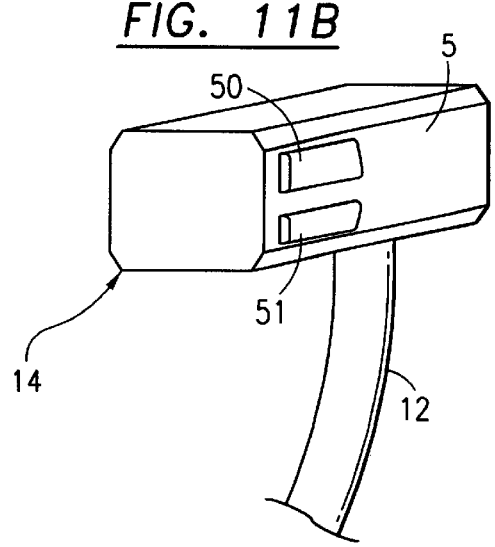
Figure 11C:
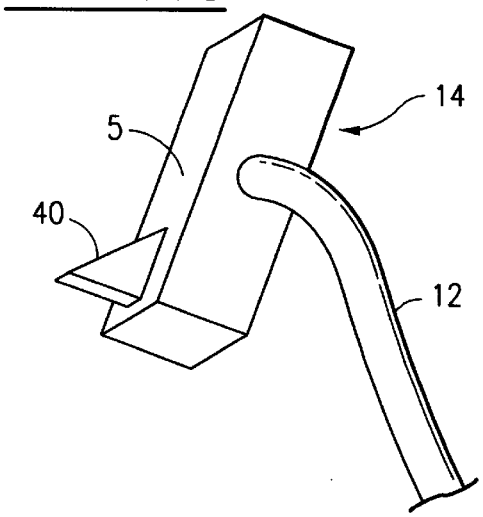

FIG. 11B shows protruding legs or arms 50, 51 protruding from side surface 5 of toggle bar 14. A plurality of legs or tabs may be utilized. FIG. 11C shows toggle 14 with a generally planar triangular tab 40 protruding from side face 5. Tab 40 in FIG. 11A is generally conical in structure with squared off surfaces. Tab 40 in FIG. 11C is generally a planar triangle.

Figure 12:
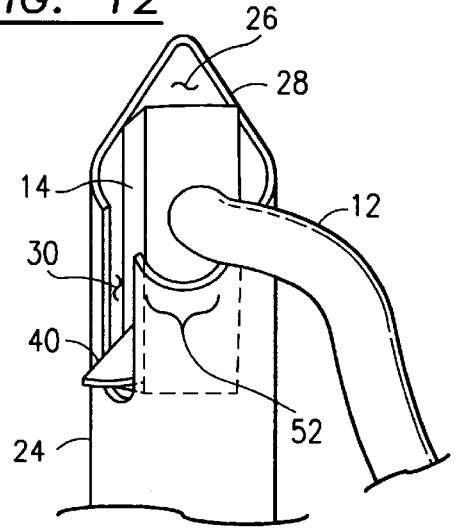
FIG. 12 diagrammatically illustrates a suture toggle deployed in a suture delivery needle.

FIG. 12 shows toggle 14 with a triangular tab deployed within the lumen of delivery needle 24. Tab 40 of toggle 14 protrudes from toggle slot 30. Suture 12 is deployed such that it exits lumen 26 of needle 24 near proximal edge region 52 of piercing terminal edge 28 of needle 24. Proximal region 52 may be rounded or smoothed to avoid cutting suture thread 12.

Figure 13A:
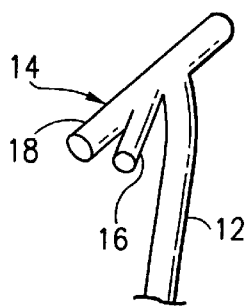
FIGS. 13A and 13B diagrammatically illustrate a toggle configured as a cylinder with a protruding side leg.
Figure 13B:
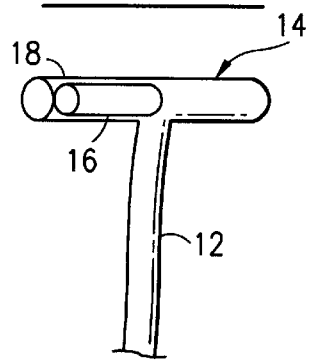

FIGS. 13A and 13B diagrammatically illustrate toggle 14 configured as a cylindrical bar with a laterally protruding leg 16. Leg 16 is also cylindrically shaped and protrudes laterally from toggle bar element 18. Leg 16 is generally normal to suture thread 12. Leg 16 is not cut from or separated from the cylindrical toggle bar.

Figure 13C:
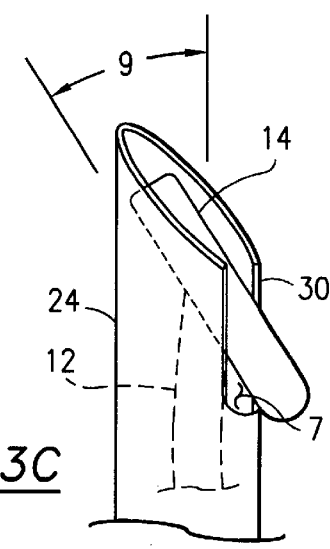
FIG. 13C diagrammatically illustrates a suture toggle configured with an angled T-bar deployed in a needle.

FIG. 13C diagrammatically illustrates toggle bar 14 at an angle 9 with respect to the axial centerline of suture thread 12. In this configuration, the acute angle 7 between angled toggle bar 14 and suture thread 12 is disposed within suture slot 30 of needle 24. This angulated configuration may enable long T-shaped bar deployment in needle 24. The term "long T-shaped" refers to the length of sides 3,5 (see FIG. 8B) relative to the cross-sectional dimension of suture thread 12. This implementation may also avoid the use of protruding legs, tabs or members.

FIGS. 14–20 diagrammatically illustrate various suture delivery systems.

FIG. 14A diagrammatically shows suture delivery system 60 which includes a basic or central tube 62 which runs over a guide wire 64. Guide wire 64 typically is not part of the suture delivery system. The illustrated delivery system in FIG. 14A is used to close puncture wounds made during catheterization. Guide wires 64 are used during such medical procedures. For purposes of explanation, suture delivery needles 66, 68 carry suture toggles and suture threads generally shown and discussed earlier in connection with FIGS. 1–13.

FIG. 15A shows suture needle 66 having a piercing edge 67 and a toggle slot 69. FIG. 15B diagrammatically illustrates a side view of suture needle 66.

Returning to FIG. 14A, base tube 62 rides over guide wire 64 in order to properly place suture needles 66, 68 on either side of arterial puncture 44 shown in FIG. 7. Suture needles 66, 68 have piercing ends 67, 67a which are laterally deployed a distance 69 from base central tube 62. In this suture delivery system, suture needles 66, 68 are made of metal having a shape memory such that when needle end segment 70 is free from needle containment or retaining structure 72, the distal ends of needles 66, 68 spring laterally outward a distance 69.

Needles 66, 68 run and protrude through needle retainer body 72 and also protrude proximally from proximal end 74 of retainer 72 towards thumb nut set 76. Proximal needle ends 75, 77 for needles 66, 68 are generally near thumb nut set 78.

Needle retention structure 72 has a proximal tube member 80 such that tube 80 runs over central tube 62. The operator moves needle retainer structure 72 by moving thumb nut set 78 in the direction shown by arrow 82. As shown in FIG. 16D, proximal tube 80 (attached to needle retainer body 72) has longitudinal slots 73a, 73b. Needles 66, 68 are attached to base or center tube 62. Hence, when tube 62 is stationary and needle retainer 72 is moved, needles 66, 68 are either exposed (FIG. 14A) or fully retained and covered (FIG. 14B).

FIG. 14B shows that needle retaining structure 72 has been pushed forward such that proximal ends 75, 77 of needles 66, 68 are proximate or near thumb nut set 78. Piercing edges 67, 67a are disposed at, near or below distal edges 79, 81 of needle retention structure 72. When the structure delivery system 60 is placed on guide wire 64 and placed near arterial puncture site 44 (FIG. 17), thumb nut set 78 (mounted on tab 80 and retainer 72) is then withdrawn in a direction opposite arrow 82 in FIG. 14A, and distal end 70 of needles 66, 68 are then exposed and sprung laterally outward due to the memory shape of the needles. The surgeon then places the distal end of tube 62 into arterial puncture 44 (FIG. 17) and continues to move delivery system 60 down guide wire 64 until he or she sees a flash of blood when piercing ends 67, 67a of needles 66, 68 pierce arterial wall 31. A flashback may also occur through base tube 62. Toggle insertion generally occurs at sites 83, 85 (FIG. 17). The surgeon then withdraws the needles thereby leaving the toggle ends of the sutures on the inside arterial wall 31. The surgeon can then close the arterial puncture after removal of guide wire 64 in a manner described above in connection with FIG. 7.

FIGS. 16A, 16B and 16C show different structures for needle retention structure 72. In FIG. 16A, retention structure 72 is generally circular in configuration. The structure contains left and right passages 82, 84 within which pass needles 66, 68. A central passage 86 permits passage of base tube 62.

In FIG. 16B, needle retention structure 72 is elliptical or oblong. In FIG. 16C, needle retention structure 72 includes a central cylindrical body 88 and two side bodies 90, 92. Side body 90 has a lumen through which passes needle 66. Side body 92 includes a lumen through which passes needle 68. Central body 88 includes a lumen through passes central or base tube 62.

FIG. 17 shows that a typical size of the large artery having dimension da which is approximately 7 mm (inside diameter) and puncture site 44 has an approximate opening size ap of approximately 2–3 mm. The lateral distance between respective piercing edges 37, 37a of needles 66, 68 is approximately 5–6 mm. The lumen of the suture toggle delivery needles 66, 68 is approximately 0.02 mm. Accordingly, the puncture for the suture toggles is small compared with the size of the arterial puncture which in turn is smaller than the inside diameter da of large artery 31.

FIG. 18 diagrammatically shows delivery system 60 including a shaped element 94 which forces needles 66, 68 to move laterally in the direction of arrows 96a and 96b outboard and away from central tube 62. Shape element 94 acts as a cam surface and needles 66,68 follow the proximal cam surface of the shape 94. The proximal end segments of needles 66,68 are attached to outer tube 80 which is further attached to screw set 78. When outer tube 80 moves forward and aft over central tube 62, the distal ends of needles 66, 68 move forward and aft over cam shape surface 94. Cam shape element 94 is mounted on central base tube 62. The following Needle Delivery Flare Table describes some shapes of the cam shape 94.

| Needle Delivery Flare Table |
|---|
| ball |
| olive |
| oblong |
| frustoconical |
| angled ribs (with apex at a proximal end) |

FIG. 19 diagrammatically shows an exploded view of delivery system 60. Thumb screw set 78 is attached to the proximal end of needle carrying tube 80. Needles 68, 68 are attached to carrying tube 80.

FIG. 20A shows needles 66, 68 from the perspective of section line 20A'–20A" in FIG. 19. The attachment of needles 66, 68 to needle carrying tube 80 is shown in a cross-sectional view in FIG. 20B from the perspective of section line 20B'–20B" in FIG. 19. The lumen 80a of needle carrying tube 80 is large enough to accommodate central tube 62. Central tube 62 extends through needle carrier tube 80.

Needles 66, 68 and needle carrying tube 80 are placed over central or base tube 62. Guide wire 64 extends through lumen 63 of central tube 62 when the system is deployed and in use.

FIG. 20C shows a cross-sectional view of central tube 62 from the perspective of section line 20C'–20C" in FIG. 19. Needle retention body 72 is mounted on central tube 62.

Needle retention body or structure 72 is mounted on central tube 62. A cross-sectional view of one embodiment of needle retention body 72 is shown in FIG. 20D. FIG. 20D is a view from section lines 20D'–20D" in FIG. 19. Needle cam shape 94 is attached to the distal end of central tube 62 slightly beyond needle exit ports 98, 99 of needle retention body 72. It should be noted that needle retention body 72 may take one or more of the shapes illustrated above in connection with FIGS. 16A, 16B and 16C.

To construct the delivery system shown in FIG. 19, needle carrying tube 80 and needles 66, 68 are placed over central tube 62. Needles 66,68 are fed into needle entrance ports 97a, 97b. Needles 66, 68 are placed into the left and right side needle lumens of needle retention structure 72 until they are proximate needle exit ports 98, 99. Thereafter, thumb nut set 76 is placed on the proximal end of central tube 62 by an appropriate attachment means (e.g., a thread). Accordingly, face 101 of set 76, along section lines 102'–102," is near or adjacent face 103 of set 78 at section lines 104'–104" which is the proximal end of thumb nut set 78. In a preferred embodiment, thumb nut set 78 may cooperate with thumb nut set 76 to lock the needle delivery system and suture delivery system together prior to deploying the system on guide wire 64. After deployment, the system takes the configuration shown above in connection with FIG. 14B except central tube 62 includes a needle cam shape 94. This cam shape is absent from FIG. 14B.

At the time of suture toggle deployment, needle carrying tube 80 is moved distally while central tube 62 remains stationary thereby causing needles 66,68 to leave exit ports 98,99 and move over needle cam surface shape 94. At that time, the distal ends of needles 66, 68 move laterally outboard (relative to the axial center line) in the direction shown by arrows 96a, 96b in FIG. 18 until the piercing surfaces of needles 66, 68 are distally beyond the needle cam shape 94. At that time, the operator inserts the distal end of central tube 62 into arterial puncture 44 shown in FIG. 17. Thereafter, needles 66, 68 pierce arterial wall 31, deposit the toggles in the artery's lumen and at the underside of arterial wall 31 and the operator withdraws the needles by moving thumb nut set 68 proximally with respect to central tube 62 which is preferably held stationary. This causes needles 66, 68 to withdraw and laterally collapse since cam surface shape 94 no longer forces the distal end of the needles to protrude laterally outward beyond central tube 62. The needles are also drawn into needle retention body 72. When the needles' terminal ends are at or near exit ports 98, 99, the entire delivery system is withdrawn and the surgeon or physician ties off the suture wire as shown in FIG. 7.

FIGS. 21–22 diagrammatically illustrate a toggle suture made of wire. This wire may be stainless steel wire. The toggle may also be memory shape metal. In contrast, the sutures discussed above in connection with FIGS. 1–13 are made of nylon or other synthetic biocompatible material.

FIG. 21A shows suture wire 110 having a wire element toggle 114 at suture terminal end 113. The wire is typically stainless steel but may be an other type of biocompatible metal material. Wire element toggle 114 includes a double strand segment 116. Wire element toggle 114 is angularly disposed, that is, disposed over angle 118a with respect to the axial central line of suture wire 110. In addition, wire element toggle 114 includes a depending wire tip section 118.

FIG. 21B shows wire element toggle 114 disposed on an inboard side of body structure, tissue or organ layer 31. Depending wire element 118 protrudes into body layer 31 thereby locking or anchoring the toggle suture in place.

FIG. 21C shows wire suture 110 with a wire element toggle 114 being normal with respect to the suture wire. The angular disposition of toggle 114 to the axial centerline of laid-out suture wire 110 is related to the needle delivery system and the spring action and toggle or latch action of the suture toggle.

FIG. 21D shows that depending leg 118 is angularly disposed at angle 121 with respect to the central axis of wire element toggle 114. The angular position is related to the needle delivery system and the degree of locking necessary on bodily structure 31.

FIG. 21E shows suture wire 110 having a wire body 122 (about 16"–18") and having toggle elements 114a, 114b attached to suture terminal ends 113a, 113b.

FIG. 21F shows wire element toggle 114 attached by welding or other type of mounting mechanism to suture terminal end 113.

FIG. 22A shows needle delivery system 124 which retains wire element toggle 114 and wire suture 112. Toggle element 114 includes an open loop 135 and a linear segment 136. Linear segment 136 rests against the proximal end wall of a needle slot 130. Open loop toggles are shown in FIGS. 21E, 22A, C and D.

FIG. 22B shows needle 124 having a toggle needle slot 130 and wire element toggle 114 having a depending leg 118 resting on toggle needle slot 130. Suture wire 110 is disposed in lumen 126 of needle 124. Leg 118 is used to mount suture wire 110 in the delivery needle. Legs 119 are shown in FIGS. 21A, 21B, 21D and 21F.

FIG. 22C shows toggle element 114 with open loop 135 disposed in toggle needle slot 130.

FIG. 22D shows wire element toggle 114 in toggle slot 130 of needle 124. Needle 124 also includes a suture slot 134 through which runs wire suture 110. Wire element toggle 114 is retained within toggle slot 130 via its open loop. The operation of the wire suture and wire element toggle is substantially similar to the suture toggle discussed above in connection with FIGS. 1–13. The operation and deployment of the suture toggle and the suture needle is also similar to that discussed above in connection with FIGS. 1–13.

Figure 23C:
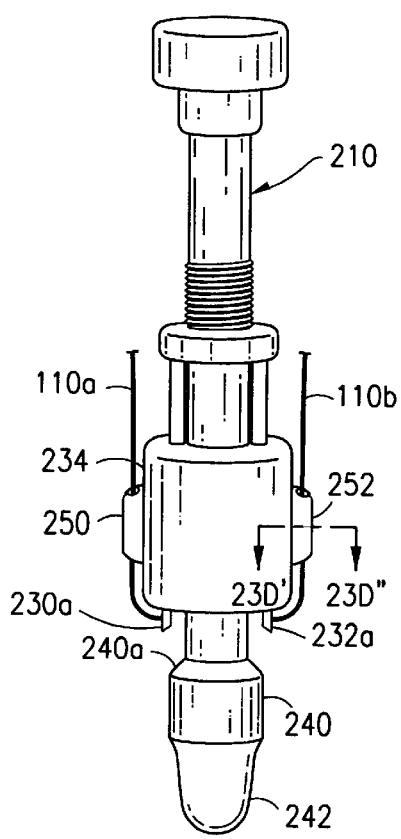
Figure 23D:
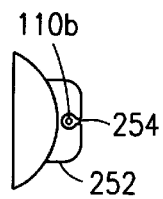
Figure 23B:
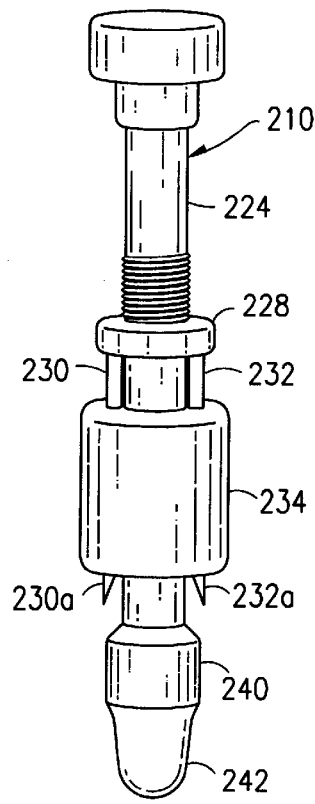

FIGS. 23A,23B and 23C diagrammatically show a delivery system 210 used in connection with fascia 220 to deploy suture toggles in a manner discussed above in connection with FIGS. 1–13 and 21–22. The deployment device shown and described in connection with FIGS. 23–24 is typically used in laparoscopic surgery. However, it maybe used whenever a surgeon needs to suture fascia.

Delivery system 210 includes handle 222 and central tube 224 which carries thread 226 at its distal end. Thread 226 coacts with threads on an inboard surface of collar 228. Collar 228 is attached to suture needles 230,232. Suture needles 230,232 move within needle passages in needle retention body 234. This mechanical theory and feature is generally discussed above in connection with needle retention body 72 and FIGS. 14A and 18.

Central body or tube 224 has a mid-section 224a and a distal section 224b. At the distal end of distal section 224b, a radially large fascia lift element 240 is mounted. A plunge cone 242 is mounted to the distal end of enlarged lift segment 240. Fascia is lifted by the proximal, peripheral radial lip 240a of lift element 240.

FIG. 23B diagrammatically shows an operational state of delivery system 210. The distal ends 230a, 232a of needles 230, 232 protrude axially beyond the distal end of needle retainer 234. In operation, the suture toggles are deposited in the fascia by rotational movement of body 224 to collar 228 translated into axial movement and needle ends 230a, 232a are withdrawn by counter rotation of central tube 224 thereby moving collar 228 in a proximal direction. Withdraw of the suture needles causes the suture toggles to remain embedded in the fascia.

FIG. 23C shows a delivery system 210 with suture wires 110a, 110b disposed outboard of suture needle ends 230a, 232a. The suture wires are run through capture channels 250,252 on either side of needle retention body 234.

FIG. 23D is a diagrammatic cross-sectional view from the perspective of section lines 23D'-23D" in FIG. 23C. Suture capture body 252 captures suture wire 110b in a channel 254. Upon deployment of the toggle suture in the fascia, the physician simply moves the suture wire outboard of the channel 254 and closes the site.

FIGS. 24A, 24B and 24C diagrammatically illustrate the operation of delivery system 210. In FIG. 24A, cone 242 and fascia support or lift element 240 have been inserted into a hole or cavity formed in fascia 220. The surgeon or physician allows the fascia to rest thereby closing the hole about distal cental rod segment 224b.

In FIG. 24B, the physician gently raises delivery system 210 in the direction shown by arrow 275. Lift element lip 240a causes fascia 220 to rise thereby lifting fascia 220 above underlying tissue elements 220a. Further, the physician rotates central handle 224 with respect to collar 228 thereby causing suture needles 230a, 232a to protrude beyond the distal end of needle retention body 234.

In FIG. 24C, the physician has completely rotated handle 224 thereby completely deploying needle ends 230a, 232a through fascia 220. Upon complete deployment of the toggle carrying sutures, the toggles engage the inboard edge or side of fascia 220 preferably in the interstitial space between underlying material 220a. The toggles are caught by the fascia, leave the toggle carrying needles, latch onto the inboard surface of fascia 220 and remain in the fascia. The surgeon then counter rotates handle 224 with respect to collar 228 thereby withdrawing suture needle ends 230a, 232a from fascia 220. Essentially, needles 230, 232 are withdrawn and recaptured by needle retention body 234. The surgeon then gently withdraws fascia lift element 240 from fascia 220. The toggles are embedded in the inboard surface of the fascia and the surgeon can then close the fascia.

Figure 25A:
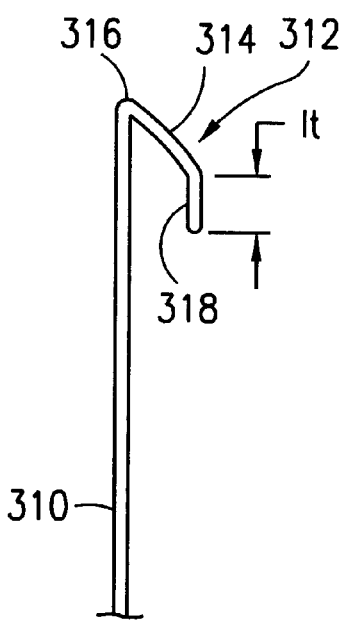
FIGS. 25A, B, C and D diagrammatically illustrate a hooked wire suture.

FIGS. 25A, B, C and D diagrammatically illustrate a wire toggle with a wire suture 310 and a wire toggle element 312. Toggle element 312 is configured as a hook with a crook or bend element 316 (0.008 or greater), an angled body segment 314 and an end segment 318. End segment 318 is generally in a plane parallel with respect to the axial centerline of wire suture 310 assuming the suture is laid out straight. The length It of hook end 318 is approximately 0.04. This configuration locks onto the inboard surface of the bodily structure after the wire suture is deployed beneath the surface. See generally FIG. 25D.

Figure 25B:
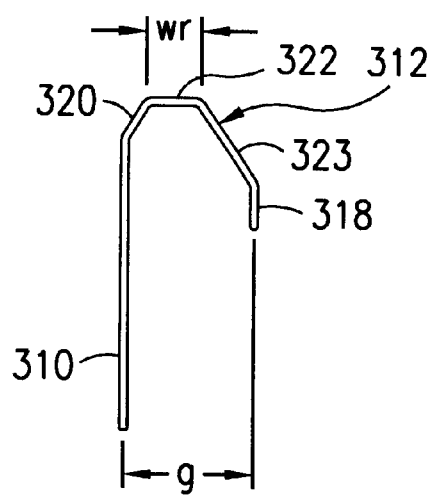
Figure 25C:
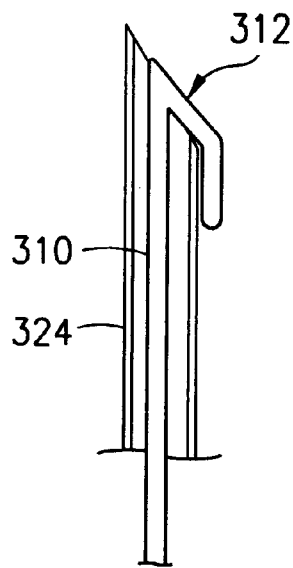

FIG. 25B illustrates toggle wire element 312 with a stepped radius or curve consisting of proximal angled segment 320, normal segment 322 (having a running length wr of about 0.020) and angled segment 323. Hook span g from suture 310 to end segment 318 is about 0.60. FIG. 25C shows hooked toggle 312 deployed in a delivery needle 324. In the illustrated embodiment, the needle does not have a suture slot.

Figure 25D:
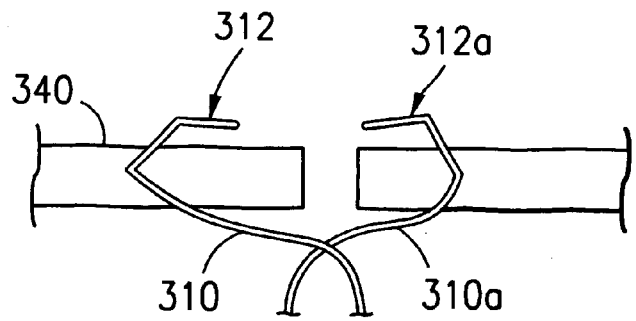

FIG. 25D illustrates the deployment of hook toggles 312, 312a and the integral or attached wire sutures 310, 310a twisted or crossed. In the configuration, the wire sutures are enabled to close the illustrated gap in body structure 340.

FIGS. 26A through 34 illustrate various suture toggles and some of the steps required to manufacture certain embodiments of the suture toggle. In the discussion that follows, a "suture toggle" refers to the suture thread together with a toggle attached at or near the suture thread's terminal end or terminal end region. A toggle is simply the toggle bar or toggle head which is attached at or near the terminal end region of the suture thread. Since some manufacturing processes utilize an end segment or end region of the thread for attachment to a toggle, the term "terminal end region" hereinafter refers to a length of suture thread at an end thereof.

FIG. 26A diagrammatically illustrates a suture toggle 10 with its toggle 14 attached to suture thread 12 such that the two define an acute angle α therebetween. Acute angle α ranges from between 25 degrees to 65 degrees. The preferred angle of toggle 14 with respect to suture thread 12 is the angle of the piercing terminal end segment 28 of suture delivery needle 24 with respect to its axial centerline (see FIGS. 2A, 2B, 4A and 4B). At the preferred angle both the toggle 14 and the piercing terminal end segment 28 are substantially parallel (see FIG. 9B). In FIG. 26A, toggle 14 has a cylindrical shape with rounded ends 22a, 22b. In FIG. 26B, suture thread 12 is disposed offset from a central region 25 of toggle 14. Toggle 14 is rectangular with chamfered or beveled edges similar to toggle 14 in FIGS. 8A. Toggle 14 may have varying characteristics, including shapes and dimensions, such that, for example, toggle 14 has a pick-like appearance with cross-sectional areas near the middle of the toggle being greater than cross-sectional areas near the ends of the toggle.

FIG. 27A diagrammatically illustrates a suture toggle 10 substantially similar to the suture toggle in FIG. 26A. The suture toggle 10 in FIG. 27A is rotated such that the toggle aligns with the longitudinal axis of suture thread 12. Note that the width of toggle 14 is slightly larger than the width of suture thread 12. FIG. 27B diagrammatically illustrates a cross-sectional view of suture toggle 10 from the perspective of section line 27B'-27B" in FIG. 27A. FIG. 27B also shows toggle 14 slightly wider than suture thread 12. Although the width of toggle 14 can be the same as the diameter of suture thread 12, in the preferred embodiment toggle 14 is slightly wider than the diameter of suture thread 12.

Toggle 14 of suture toggle 10 illustrated in FIGS. 26A through 27B may include an extending leg, a protruding leg or a protruding tab, as discussed above in connection with FIGS. 1A through 13C. In addition, suture toggle 10 in FIGS. 26A through 27B functions substantially similar to suture toggle 10 discussed above in connection with FIGS. 1A through 13C.

FIGS. 28A through 28G2 illustrate components of suture toggle 10 and some of the steps necessary for its manufacture. FIG. 28A diagrammatically illustrates toggle 14 having an elongated cylindrical shape with ends 22a, 22b being substantially perpendicular to longitudinal axis line 32. Ends 22a, 22b can be rounded or include protrusions. FIG. 28B1 diagrammatically illustrates toggle 14 defining a channel 410 with a channel face 420. Channel 410 extends from approximately the center of elongated toggle 14 to end 22a which defines a channel mouth 416. In FIG. 28B1, channel 410 is shallow near the middle of toggle 14 and deeper at the channel mouth region 416. Channel 410 may include other configurations. For example, channel 210 may have substantially the same dimension as channel mouth 416 throughout. FIG. 28B2 diagrammatically illustrates a cross-sectional view of toggle 14 from the perspective of 28B2'–28B2" in FIG. 28B1. FIG. 28C diagrammatically illustrates toggle 14 including channel 410 with channel face 420. Channel face 420 includes score marks, grooves or ridges 418 making the surface of channel face 420 rough. FIG. 28D depicts suture thread 12 with end segment 17 and terminal end face 23. Suture thread 12 is dangling over vat 434 containing a liquid polymer or other biocompatible coating material 430.

FIG. 28E diagrammatically illustrates toggle 14 with a portion of the end segment 17 of a suture thread 12 positioned within channel 410 of the toggle. End segment 17 of suture thread 12 is stiff. FIG. 28F1 diagrammatically illustrates toggle 14 with a portion of the end segment of suture thread 12 swaged within channel 410 of toggle 14, thus forming a closed channel thereat. Channel walls 414a, 414b are illustrated partially encircling the aforementioned portion of suture thread 12. FIG. 28F2 diagrammatically illustrates a partial, side or end view of toggle 14 and suture thread 12. Terminal end face 23 of suture thread 12 and a portion of its end segment are caught within closed channel 410 of toggle 14. Channel walls 414a, 414b encircle suture thread 12 such that the suture thread is trapped within toggle 14. Channel walls 414a, 414b can be formed long enough to come in contact with each other or overlap at region 412. Note that in FIG. 28F2 suture thread 12 has a diameter slightly smaller than the diameter of toggle 14.

FIG. 28G1 illustrates toggle 14 and end segment 17 of suture toggle 10 being sprayed by a polymer, poly-acetate, biocompatible acrylic (cyno-acrylic) or other biocompatible material 440. FIG. 28G2 illustrates suture toggle 10 prior to being immersed in a vat 434 filled with a polymer, a poly-acetate or a biocompatible material 440. The suture thread end is stiffened in a cold dip, lower than the suture thread melt point or flow point.

FIG. 29A diagrammatically illustrates a hollow, elongated toggle 14 defining a longitudinal passage 436 and a hole 444. Toggle 14 may be made of a metallic material such as an nitinol or stainless steel, or may be made of any biocompatible material. The illustration of suture thread 12 and vat 434 in FIG. 29B1 is substantially similar to the illustration in FIG. 28D. FIG. 29B2 illustrates one method of stiffening end segment 17 of suture thread 12. End segment 17 of suture toggle 10 is lying on surface 442 and being sprayed by a polymer, poly-acetate or biocompatible material 440.

FIG. 29C diagrammatically illustrates terminal end region 19 of suture thread 12 near end 22b of toggle 14. Wedge mandrel 446 is shown with wedged end 448 adjacent end 22a of toggle 14. FIG. 29D1 diagrammatically illustrates toggle 14 with a portion of suture thread 12 inserted in passage 436 at end 22b and wedge mandrel 446 inserted at the other end of passage 436 at end 22a. FIG. 29D2 diagrammatically illustrates a partial cross-sectional view of toggle 14, suture thread 12 and wedge mandrel 446 illustrated in FIG. 29D1. The terminal end face 23 of suture thread 12 abuts the tip of mandrel 446.

Figure 30A:
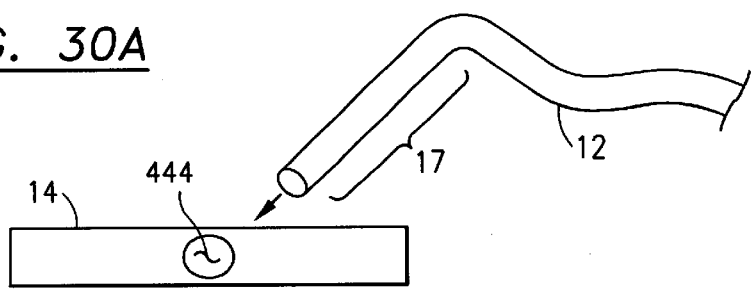
FIGS. 30A, 30B and 30C diagrammatically illustrate the steps in a further alternative method of manufacturing a suture toggle.
Figure 30B:
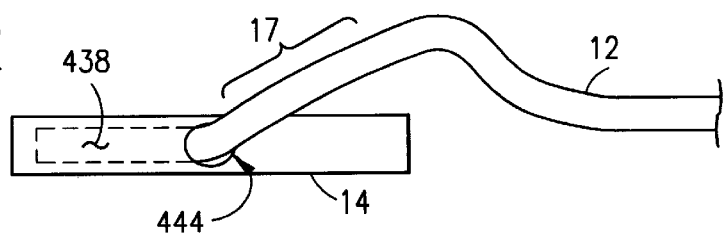
Figure 30C:
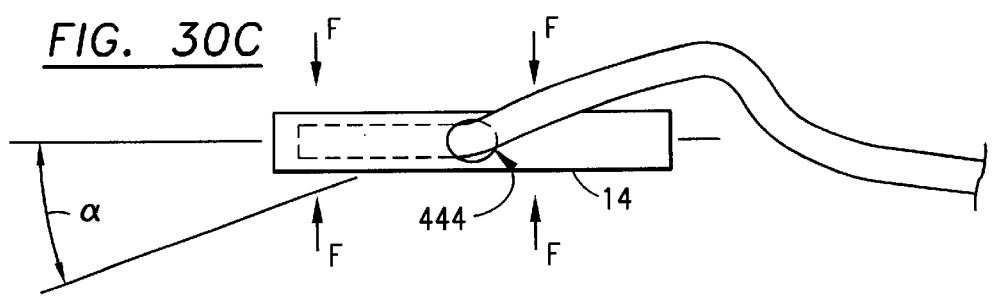
Figure 31A:
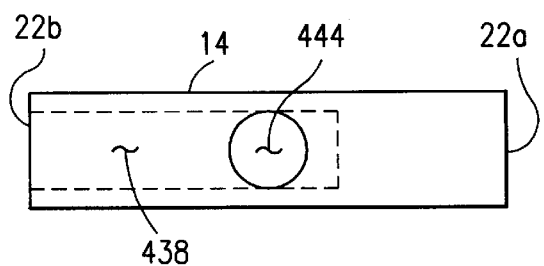
FIGS. 31A and 31B diagrammatically illustrate alternative embodiments of a toggle for the suture toggle.
Figure 31B:
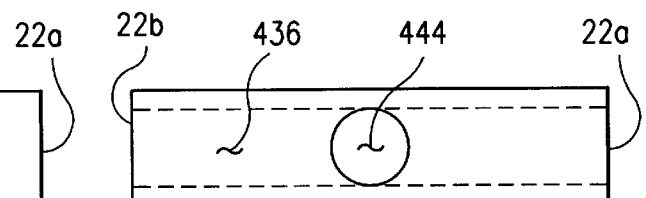

FIG. 30A diagrammatically illustrates a suture thread 12 with stiffened end segment 17 positioned to be inserted into hole 444 on toggle 14. FIGS. 30B and 30C illustrate toggle 14 with a portion of stiffened end segment 17 of suture thread 12 inserted into hole 444 and lying within a cavity or a passage 438 of toggle 14. The portion of stiffened end segment 17 of suture thread 12 lying outside of toggle 14 and the longitudinal axis of toggle 14 define an acute angle α. FIGS. 31A and 31B diagrammatically illustrate alternative embodiments of toggle 14. Toggle 14 in FIG. 31A includes a passage 438 running from end 22b to hole 444. Toggle 14 in FIG. 31B includes a longitudinal passage 436 running the length of toggle 14 with hole 444 communicating with longitudinal passage 436.

Figure 32:
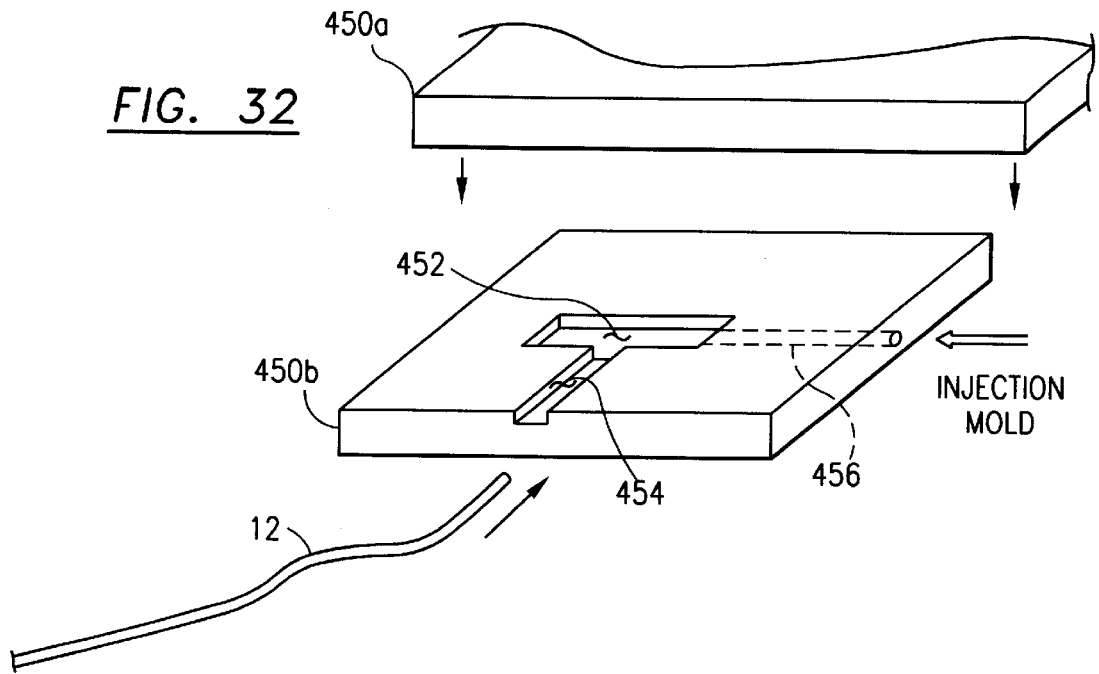
FIG. 32 diagrammatically illustrates an alternative method of manufacturing a suture toggle.

FIG. 32 diagrammatically illustrates a mold die 450a, 450b defining a toggle-shaped cavity 452 and a suture thread-shaped cavity 454 communicating therewith. Mold die 450a, 450b is illustrated as two plates. However, the mold die can consist of any number of plates, including a single piece. In addition, mold 450 may also include a protruding member-shaped cavity communicating with the toggle cavity 452. In FIG. 32, mold plate 450b includes an injection mold port 456 communicating with toggle cavity 452.

Figure 33:
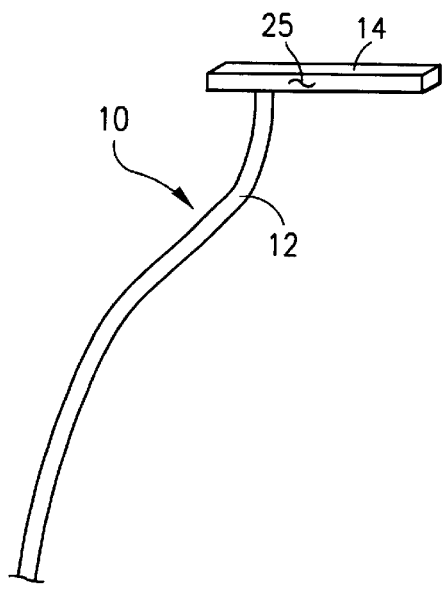
FIG. 33 diagrammatically illustrates a suture toggle with an eccentrically mounted toggle.
Figure 34:
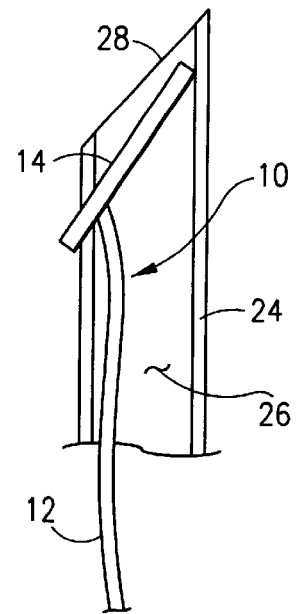
FIG. 34 diagrammatically illustrates a suture toggle with an eccentrically mounted toggle, mounted within a delivery needle.

FIG. 33 diagrammatically illustrates suture toggle 10 with rectangular-shaped toggle 14. Suture thread 12 is disposed offset from central region 25 of toggle 14. FIG. 34 diagrammatically illustrates suture toggle 10 loaded within the lumen 26 of delivery needle 24. The elongated toggle 14 is substantially parallel to piercing end 28 of needle 24.

One embodiment of the suture toggle 10 is manufactured by the following method in which toggle 14 is swaged onto the suture thread 12 or suture thread 12 is swaged within toggle 14. The swaged toggle is crushed or closed about 0.002 inches from original size. The first step includes preparing a toggle 14 to receive a suture thread 12. As shown in FIG. 28B1, a channel or cutout must be created on toggle 14. Channel or cutout 410 can be created by boring away a portion of toggle 14, cutting toggle 14 either by mechanical means or a laser, by grinding toggle 14, by molding toggle 14, or by forming toggle 14. At least a portion of the toggle must define a channel or cutout within which a suture thread will fit. The channel can be a groove, slit or similar opening sufficient to accommodate a portion of the end segment 17 of the suture thread. Determination of the location of channel 410 depends upon the ultimate location of suture thread 12 relative to toggle 14. If suture thread 12 is to be substantially, centrally attached to toggle 14 (e.g., see FIGS. 1A, 5A and 26A), then channel 410 must include an open side region capable of accommodating an end segment of the suture thread located at or near the center of toggle 14. In the same vein, if suture thread 12 is to be disposed offset from central region 25 of toggle 14 (e.g., see FIGS. 2B, 5C, 26B and 33), then the open side region should be located at or near the desired location on the toggle to form the connection between the toggle and thread.

The channel or cutout 410 defined by toggle 14 may then be roughened as shown in FIG. 28C. The roughening may be accomplished during the process utilized to create the channel or thereafter. For example, if the channel is formed using a drill, the drill bit utilized may leave channel face 420 rough. The channel surface 420 may also be scored or roughened through use of an abrasive, a tumble-stone process, or by cutting ridges 418 into the toggle material. Although the roughening step is not required, it is preferred. The roughening of channel surface 420 enhances the friction or grip between the toggle surface and suture thread once the suture thread 12 is attached to the toggle 14.

Prior to positioning the suture thread 12 in channel 410, an end segment of suture thread 12 should be stiffened. Stiffening of end segment 17 can be accomplished by cold dipping or immersing end segment 17 in a polymer or biocompatible material (see FIG. 28D). The temperature of the cold dip material 430 should be lower than the melting point or flow point of the suture thread. Alternatively, end segment 17 can be stiffened by spraying the segment with a biocompatible acrylic or other biocompatible stiffening agent (see FIG. 29B2). The suture thread 12 is placed on a flat surface 442 (FIG. 29B2) and sprayed with a biocompatible stiffening material 440. The suture thread 12 is rolled as indicated by arrow 460 in order to coat the surface of end segment 17 of suture thread 12. The suture thread is then allowed to dry enabling the coating material to cure, dry or cool.

A portion of the stiffened end segment 17 of suture thread 12 is placed in channel 410 (see FIG. 28E). The suture thread end segment 17 should be positioned such that the portion of the stiffened end segment outside the channel 410 forms the desired acute angle α relative to the longitudinal axis of toggle 14. Of course, the suture may also be placed such that the suture thread 12 and toggle 14 form a right angle or are perpendicular with respect to each other.

After placing the portion of stiffened suture thread end segment 17 within channel 410, the toggle channel 410 is swaged closed about that portion. In FIG. 28E, swaging is accomplished by application of a force to toggle 14 in the direction of arrows F. In FIG. 28F 1, channel walls 414a, 414b of toggle 14 have been swaged about a portion of stiffened end 17. Toggle 14 or channel 410 can be formed such that the swaging produces overlapping channel walls 414a, 414b. After swaging, toggle 14 may become deformed to create a new shape. Toggle 14 and channel 410 defined thereby may be designed to form a predetermined shape upon completion of the swaging step.

After swaging, the toggle 14 and suture thread end segment 17 may be coated with a polymer or biocompatible material 440 in either of the two manners described above in connection with stiffening of the suture thread. Prior to the coating process, or prior to the swaging process, the toggle may be roughened in order to enhance the bonding of the coating to the toggle surface. Such roughening may be accomplished with an abrasive, as described earlier in connection with roughening of the channel surface, or with plasma. The suture toggle 10 is exposed to hot gas which cleans the surfaces of the suture thread and toggle of impurities and roughens the surfaces.

Another embodiment of the suture toggle 10 is manufactured by the following process. An elongated toggle 14 is bored along its longitudinal axis, thereby creating a longitudinal passage through the toggle. The passage can traverse the entire toggle (see FIGS. 29A and 31B) or a portion necessary for attachment of a suture thread (see FIG. 31A). A hole 444 is then bored into the side of the elongated toggle. The location of hole 444 will determine the attachment location of suture thread 12 relative to toggle 14. Again, passage 436 and hole 444 can be created using numerous processes or a combination of them, including those discussed in connection with creation of the channel or cutout on toggle 14.

In one embodiment, an end segment 17 of suture thread 12 is stiffened in the same manner as discussed above in connection with thread 12 of the swaged suture toggle 10. If the passage 436 traverses the entire toggle, then the non-stiffened end is inserted into one end of toggle 14 and wedge mandrel 446 into the other end as illustrated in FIGS. 29C, 29D1 and 29D2. Mandrel 446 forces end region 19 of suture thread 12 through hole 444 on toggle 14. The length of suture thread 12 is then run through the passage until a portion of the stiffened end segment 17 is within passage 436 and a portion protrudes from hole 444. The toggle passage 436 is swaged about the portion of end segment 17 lying therein (see FIG. 30C). If the passage 436 traverses only a portion of toggle 14 as shown in FIG. 30B, for example, then the stiffened suture thread end segment 17 is inserted through hole 444 and into passage 436. Subsequently, the same swaging force is applied to capture a portion of the suture thread 12 within toggle 14. Again, in this alternative embodiment, it is preferred that the toggle be coated with a biocompatible coating as described earlier in connection with the swaged suture toggle including a channel.

Another embodiment of the suture toggle 10 is manufactured by the following molding process. A mold die is created having the desired dimensions and characteristics of the particular toggle shape to be manufactured. For example, a toggle 14 having protruding tabs or an extending leg would require a toggle cavity 452 with a cavity for the protruding member or extending leg communicating therewith. In FIG. 32, mold die 450a, 450b defines a toggle-shaped cavity 452 and a suture thread-shaped cavity 454 communicating therewith, but does not include a protruding member cavity. Next, a suture thread 12 is inserted in the mold die such that when the toggle is formed it will be disposed on the suture thread. In the preferred embodiment, an end segment 17 of suture thread 12 is stiffened. The stiffening of end segment 17 may be accomplished prior to molding toggle 14 by one of the steps discussed earlier in connection with manufacturing of the swaged suture toggles, or may be accomplished during the molding process. Upon inserting a portion of suture thread 12 into the suture thread cavity 454, toggle 14 is molded by conventional means as known in the art. For example, a liquified polymer is injected into injection mold port 456. After the molding process is complete, suture toggle 10 is removed from die 450a, 450b. In the preferred embodiment, either the material used to form toggle 14 or the molding process, or a combination thereof, will result in toggle 14 being stiffer or having a higher durometer measurement than suture thread 12.

The claims appended hereto are meant to cover modifications and changes within the scope and spirit of the present invention.

What is claimed is:

1. A method of manufacture for producing a suture toggle from a suture thread having an end segment at a terminal end thereof, and a toggle comprising the steps of:
   creating at least a partial channel on said toggle;
   stiffening the suture thread end segment;
   positioning a portion of the stiffened end segment in said channel;
   swaging said toggle channel closed about said portion of said stiffened end segment; and,
   roughening said suture channel in said toggle after said creating step.

2. A method of manufacture for producing a suture toggle from a suture thread having an end segment at a terminal end thereof, and a toggle comprising the steps of:
   creating at least a partial channel on said toggle;
   stiffening the suture thread end segment;
   positioning a portion of the stiffened end segment in said channel;
   swaging said toggle channel closed about said portion of said stiffened end segment; and
   wherein said stiffening step includes one of cold dipping said suture thread end segment into a polymer and spraying said suture thread end segment with a biocompatible acrylic.

3. A method as claimed in claim 2 further comprising the step of drying said stiffened end segment prior to said positioning step.

4. A method of manufacture for producing a suture toggle from a suture thread having an end segment at a terminal end thereof, and a toggle comprising the steps of:
creating at least a partial channel on said toggle;
stiffening the suture thread end segment;
positioning a portion of the stiffened end segment in said channel;
swaging said toggle channel closed about said portion of said stiffened end segment; and,
coating said toggle and said suture thread end segment with a biocompatible polymer after said swaging step.

5. A method of manufacture for producing a suture toggle from a suture thread having an end segment at a terminal end thereof and an elongated toggle having a longitudinal axis comprising the steps of:
creating a longitudinal passage through said toggle;
forming a lateral hole through said toggle and into said passage;
stiffening the suture thread end segment;
placing said suture thread in said passage and through said hole such that a portion of the stiffened end segment lies in said passage and protrudes from said hole;
swaging the toggle closed about the captured stiffened end segment; and
coating said toggle and said portion of said stiffened end segment with a biocompatible material.

6. A method as claimed in claim 5 wherein said creating step and said forming step include cutting said toggle with a laser.

7. A method as claimed in claim 5 further comprising the step of roughening said toggle after one of said creating step and said forming step.

8. A method as claimed in claim 5 wherein said placing step includes aligning said stiffened end segment and said toggle to define an acute angle therebetween.

9. A method as claimed in claim 5 wherein said stiffening step includes one of cold dipping said suture thread end segment into a polymer and spraying said suture thread end segment with a biocompatible acrylic.

10. A method as claimed in claim 9 further comprising the step of drying said stiffened end segment prior to said placing step.

11. A method of manufacture for producing a suture toggle with a suture thread having an end segment at a terminal end thereof comprising the steps of:
providing a mold defining a toggle-shaped cavity and a suture thread-shaped cavity communicating therewith;
stiffening the suture thread end segment;
positioning said suture thread end segment within said suture thread cavity;
molding a toggle onto the positioned suture thread end segment at an acute angle with said mold.

12. A method as claimed in claim 11 wherein said acute angle is between 25 degrees and 65 degrees.

13. A method as claimed in claim 11 wherein said stiffening step includes one of cold dipping said suture thread end segment into a polymer and spraying said suture thread end segment with a biocompatible acrylic.

14. A method as claimed in claim 13 further comprising the step of drying said stiffened end segment prior to said attaching step.

15. A method as claimed in claim 11 wherein said mold in said providing step defines a toggle cavity having one of a cylindrical shape, a rectangular shape and a rectangular shape with beveled edges.

16. A method as claimed in claim 11 wherein said positioning step occurs prior to said stiffening step and said stiffening step occurs substantially concurrently with said molding step.

17. A method as claimed in claim 11 wherein said toggle cavity includes a cavity defining a protruding member communicating therewith.

18. A method of manufacture for producing a suture toggle with a suture thread having an end segment at a terminal end thereof comprising the steps of:
providing a mold defining a toggle-shaped cavity, a suture thread-shaped cavity and a protruding member-shaped cavity, the suture thread and protruding member cavities communicating with the toggle cavity;
stiffening the suture thread end segment;
positioning said suture thread end segment within said suture thread cavity; and
molding a toggle with a protruding member onto the positioned suture thread end segment with said mold.

19. A method as claimed in claim 18 wherein said molding step includes molding said toggle with said protruding member onto said positioned suture thread end segment at an acute angle.

20. A method as claimed in claim 19 wherein said acute angle is between 25 degrees and 65 degrees.

21. A method as claimed in claim 18 wherein said stiffening step includes one of cold dipping said suture thread end segment into a polymer and spraying said suture thread end segment with a biocompatible acrylic.

22. A method as claimed in claim 18 further comprising the step of drying said stiffened end segment prior to said attaching step.

23. A method as claimed in claim 18 wherein said mold in said providing step defines a toggle cavity having one of a cylindrical shape, rectangular shape and a rectangular shape with beveled edges.

24. A method as claimed in claim 18 wherein said positioning step occurs prior to said stiffening step and said stiffening step occurs substantially concurrently with said molding step.

* * * * *